Figure 1:
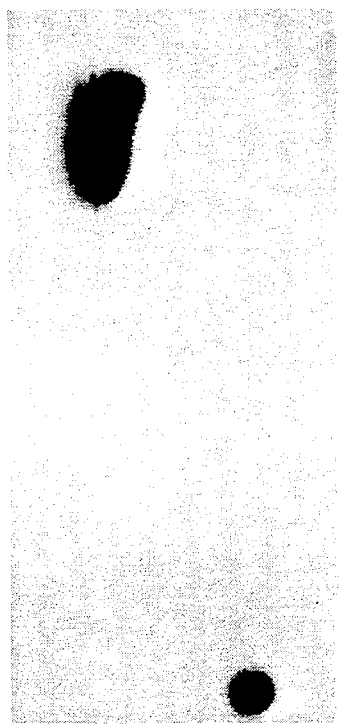

United States Patent [19]

Coughlin et al.

[11] Patent Number: 5,326,856
[45] Date of Patent: Jul. 5, 1994

[54] BIFUNCTIONAL ISOTHIOCYANATE DERIVED THIOCARBONYLS AS LIGANDS FOR METAL BINDING

[75] Inventors: Daniel J. Coughlin, Robbinsville; Benjamin A. Belinka, Jr., Kendall Park, both of N.J.

[73] Assignee: Cytogen Corporation, Princeton, N.J.

[21] Appl. No.: 866,375

[22] Filed: Apr. 9, 1992

[51] Int. Cl.$^5$ .................. C07C 337/06; C07C 335.22; C07D 207/44; C07D 213/71
[52] U.S. Cl. ...................... 534/14; 534/10; 530/300; 530/391.5; 530/408; 564/18; 564/23; 564/26; 564/27; 564/28; 556/45; 556/64; 556/81; 556/110; 556/118; 560/18; 562/432; 536/26.6; 552/502; 552/504
[58] Field of Search .................... 424/1.1; 534/10, 14; 530/391.1, 391.5, 300, 408; 536/22.1, 26.6; 554/502; 556/45, 110, 118, 81, 64; 560/9.18; 562/432; 564/18, 23, 26, 27, 28

[56] References Cited

U.S. PATENT DOCUMENTS

| 4,048,326 | 9/1977 | Berg et al. ...................... 560/16 X |
| 4,060,636 | 11/1977 | Kilbourn et al. ................... 514/584 |
| 4,072,696 | 2/1978 | Beard et al. ...................... 560/16 X |
| 4,086,235 | 4/1978 | Beard .................................... 560/16 |
| 4,287,362 | 9/1981 | Yokoyama et al. .................... 424/1.1 |
| 4,732,864 | 3/1988 | Tolman et al. ........................ 424/1.1 |
| 4,732,974 | 3/1988 | Nocolotti et al. .................... 424/1.1 |
| 5,078,985 | 1/1992 | Rhodes ................................ 424/1.1 |
| 5,080,884 | 1/1992 | McBride et al. ...................... 424/1.1 |
| 5,101,041 | 3/1992 | Troutner et al. .................... 548/518 |
| 5,116,596 | 5/1992 | Bremer et al. ........................ 424/1.1 |

FOREIGN PATENT DOCUMENTS

| 0137457A2 | 4/1985 | European Pat. Off. . |
| 173424A1 | 3/1986 | European Pat. Off. . |
| 0188256A2 | 7/1986 | European Pat. Off. . |
| 247866A1 | 12/1987 | European Pat. Off. . |
| 0306168A1 | 3/1989 | European Pat. Off. . |
| WO8704164 | 7/1987 | PCT Int'l Appl. . |
| WO8807382 | 10/1988 | PCT Int'l Appl. . |
| WO8912625 | 12/1989 | PCT Int'l Appl. . |
| 1307250 | 2/1973 | United Kingdom . |

OTHER PUBLICATIONS

Arano et al., "Synthesis and Evaluation of a New Bifunctional Chelating Agent for $^{99m}$Tc Labeling Proteins: p-Carboxyethylphenylglyoxal-di(N-methylthiosemicarbazone)", Int. J. Nucl. Med. Biol. 12:425–430 (1986).

Arano et al., "Technetium-99m-Labeled Monoclonal Antibody With Preserved Immunoreactivity and High In Vivo Stability", J. Nucl. Med. 28:1027–1033 (1987).

Collen et al., "Thrombolysis with human extrinsic (tissue-type) plasinogen activator in Rabbits with experimental jugular vein thrombosis", J. Clin. Invest. 71:368–376 (1983).

Eckelman et al., "Three Approaches to Radiolabeling Antibodies with $^{99m}$Tc", Nucl. Med. Biol., 16(2):171–176 (1989).

Fritzberg, et al., "Specific and Stable Labeling of Antibodies With Technetium-99m With a Diamide Dithiolate Chelating Agent", Proc. Natl. Acad. Sci. U.S.A. 85:4025–4029 (1988).

Huang et al., "Detection of bacterial endocarditis with Technetium-99m-labeled antistaphylococcal antibody", J. Nucl. Med. 21:783–786 (1980).

Hull, "An Improved preparation of O-phenylenedi isothiocyanate", Synthetic Commun. 9:477–481 (1979).

Kopunec et al., "Reaction of Pertechnetate With Thiourea in the Nitric Acid Solutions", Radiochem. Radioanal. Lett. 29:171–178 (1977).

(List continued on next page.)

Primary Examiner—Robert L. Stoll
Assistant Examiner—John M. Covert
Attorney, Agent, or Firm—Oblon, Spivak, McClelland, Maier & Neustadt

[57] ABSTRACT

This invention relates to chelating agents useful for coupling metal ions to biologically active molecules. In particular, isothiocyanate derived thiocarbonyls for chelating metals such as technetium are provided that can be conjugated to a targeting molecule such as an antibody, a peptide or a protein.

45 Claims, 11 Drawing Sheets

OTHER PUBLICATIONS

Lever et al., "Synthesis of a Novel Bifunctional Chelate Designed for Labeling Proteins With Technetium$^{99mn}$", Tetrahedron Letters 29 (26):3219–3222 (1988).

Misra et al., "Synthesis of a Novel Diaminodithiol Ligand for Labeling Proteins and Small Molecules With Technetium$^{99m}$", Tetrahedron Lett., 30(15): 1885–1888 (1989).

Pinkerton et al., "Bioinorganic activity of technetium pharmaceuticals", J. Chem. Educ. 62:965–973 (1985).

Rhodes et al., in "Tumor Imaging", Burchiel and Rhodes, eds., Masson: New York, pp. 111–123, (1982).

Schwartz et al., "Preparation of Hydrazino-Modified Proteins and Their Use for the Synthesis of $^{99m}$Tc–Protein Conjugates", Bioconjugate Chem. 2:333–336 (1991).

Sundrehagen, "Formation of $^{99m}$Tc-immunoglobulin G complexes free from radiocolloids, quality controlled by radioimmunoelectrophoresis", Eur. J. Nucl. Med. 7:549–552 (1982).

Wensel et al., "Bifunctional Chelating Agents for Binding Metal Ions to Proteins", in Radioimmunoimaging and Radioimmunotherapy, Burchiek and Rhodes (eds.), Elsevier Science Publishing, Inc., pp. 185–196 (1983).

Zucker, "Platelet aggregation measured by the photometric method", Meth. Enzymol. 169:117–133 (1989).

E. Leiber et al., "Diisothiocyanates and Derivatives", Journal of Organic Chemistry, vol. 27, No. 6, Jun. 12, 1962, pp. 2214–2217.

E. Cullen et al., "Bis Basic Substituted Diaminobenzobisthiazoles as Potential Antiarthritic Agents", Journal of Medicinal Chemistry, vol. 35, No.2, Jan. 24, 1992, pp. 350–361.

Y. Arano et al., "Bifunctional Chelating Agents For 99Tcm-Labelled Monoclonal Antibodies", IAE-A-C-N-45/68, pp. 143–151.

Y. Arano et al., "In the Procurement of Stabel 99mTc Labeled Protein Using Bifunctional Chelating Agents", Appl. Radiat. Isot., vol. 37, No. 7, pp. 587–592, 1986.

Arano et al., "Synthesis and Evaluation of a New Bifunctional Chelating Agent for Tc$^{99m}$ Labeling Proteins: p-Carboxyethylphenylglyoxal-di(N-methylthiosemicarbazone)", Int J. Nucl. Med. Biol., 12: 425–430 (1986).

RETENTION TIME (MINUTES)

BIFUNCTIONAL ISOTHIOCYANATE DERIVED THIOCARBONYLS AS LIGANDS FOR METAL BINDING

TABLE OF CONTENTS

1. FIELD OF THE INVENTION
2. BACKGROUND OF THE INVENTION
3. SUMMARY OF THE INVENTION
4. BRIEF DESCRIPTION OF THE DRAWINGS
5. DETAILED DESCRIPTION OF THE INVENTION
   5.1. BIFUNCTIONAL DIISOTHIOCYANTE DERIVATIVES
      5.1.1. DIISOTHIOCYNATES AND PREPARATION THEREOF
      5.1.2. REAGENTS FOR ADDITION TO THE DIISOTHIOCYANATES
      5.1.3. REACTION OF DIAMINES WITH ISOTHIOCYANATE DERIVATIVES
   5.2. LINKER GROUPS
      5.2.1. ATTACHMENT TO OXIDIZED CARBOHYDRATE MOIETIES
      5.2.2. ATTACHMENT TO SULFHYDRYL GROUPS
      5.2.3. ATTACHMENT TO AMINO OR CARBOXY GROUPS OF A PROTEIN
      5.2.4. LINKERS FOR CONJUGATION WITH NON-PROTEIN TARGETING MOLECULES AND SUPPORTS
   5.3. PREPARATION OF COMPLEXES
   5.4. USES OF TARGETING MOLECULE - CHELATING AGENT - METAL ION COMPLEXES
      5.4.1. IN VIVO THERAPEUTICS
      5.4.2. IN VIVO DIAGNOSTICS
      5.4.3. IN VITRO DIAGNOSTICS
   5.5. PHARMACEUTICAL COMPOSITIONS
6. EXAMPLE: PREPARATION OF 3,5-DI-(1-TRIMETHYLAMMONIUMACETYL)-4-THIOSEMICARBAZIDOBENZOIC ACID, DICHLORIDE SALT (CHELATING AGENT A)
   6.1. 3,5-DIISOTHIOCYANATOBENZOIC ACID
   6.2. CHELATING AGENT A
7. EXAMPLE: PREPARATION OF A HYDRAZIDE LINKER ANALOG-OF CHELATING AGENT A (CHELATING AGENT B)
   7.1. PREPARATION OF N-BOC-6 AMINOCAPROIC ACID
   7.2. PREPARATION OF N-BOC-6-AMINOCAPROIC ACID, N'-FMOC(FLOURENYLMETHOXYCARBONYL)HYDRAZIDE
   7.3. PREPARATION OF 6-AMINOCAPROIC ACID N'-FMOC HYDRAZIDE
   7.4. PREPARATION OF THE 6-AMINOCAPROIC ACID, N'-FMOC HYDRAZIDE DERIVATIVE OF CHELATING AGENT A
   7.5. PREPARATION OF CHELATING AGENT B
8. EXAMPLE: PREPARATION OF 3,4 -DI- (1-METHYLTHIOFORMAMIDO)-4-THIOSEMICARBAZIDOBENZOIC ACID, METHYL ESTER (CHELATING AGENT C)
   8.1. PREPARATION OF 5-BENZIMIDAZOLECARBOXYLIC ACID, METHYL ESTER
   8.2. PREPARATION OF 3,4-DIISOTHIOCYANATOBENZOIC ACID, METHYL ESTER
   8.3. PREPARATION OF CHELATING AGENT C
9. PREPARATION OF A PEPTIDE CONJUGATE AND ISOTOPE LABELING
   9.1. COUPLING OF CHELATING AGENT A WITH SYRGDVRGDF-NH$_2$ PEPTIDE
   9.2. LABELING OF PEPTIDE CONJUGATE WITH TC-99M
   9.3. RESULTS OF RADIOLABELING
10. EXAMPLE: PREPARATION AND Tc-99m RADIOLABELING OF AN ANTIBODY CONJUGATE
    10.1. MATERIALS AND METHODS
       10.1.1. OXIDATION PROCEDURE
       10.1.2. CONJUGATION PROCEDURE
       10.1.3. Tc-99m RADIOLABELING PROCEDURE
    10.2. RESULTS
11. EXAMPLE: BIODISTRIBUTION OF Tc-99m-LABELED CHELATORS
12. EXAMPLE: IMAGING OF A TUMOR WITH TC-99M-LABELED ANTIBODY
    12.1. MATERIALS AND METHODS
    12.2. RESULTS
    12.3. CONCLUSION
13. EXAMPLE: THROMBUS IMAGING WITH A PEPTIDE-CHELATING AGENT A CONJUGATE
    13.1. MATERIALS AND METHODS
    13.2. RESULTS
    13.3. CONCLUSIONS

1. FIELD OF THE INVENTION

This invention relates to chelating agents useful for coupling metal ions to biologically active molecules.

2. BACKGROUND OF THE INVENTION

It has been discovered that antibodies and certain peptides can be used as highly specific vehicles for the delivery of drugs or radioisotopes to target organs, tumors or thrombi in vivo. Methods have been reported for the direct labeling of antibodies with radioisotopes (Huang et al., 1980, J. Nucl. Med. 21:783; Rhodes et al., in "Tumor Imaging", Burchiel and Rhodes, eds., Masson: New York, p. 111, 1982; and Sundrehagen, 1982, Eur. J. Nucl. Med. 7:549), taking advantage of partial reduction of protein disulfide linkages to generate free thiol groups capable of binding radiometals such as technetium. Because not all proteins or especially peptides contain readily reducible disulfides and partial reduction may alter the biological activity relative to the native molecule, it would be desirable to utilize a bifunctional radiometal chelator to form a covalent radiometal-chelator-peptide/protein conjugate capable of targeting radiometals in-vivo.

Of particular interest in nuclear medicine is the radiometal technetium-99m. Technetium is one of a class of metal ions that form strong coordinate bonds with sulfur-containing compounds, particularly thiols (e.g., metallothionine), but also thiourea. Kopunec et al. (1977, Radiochem. Radioanal. Lett. 29:171) describe the binding of technetium by thioureas to form complexes. This illustrates that thiocarbonyl functional groups bind technetium and thus may be useful as one part of a technetium binding bifunctional chelator. Technetium is a preferred isotope for scintigraphic imaging applications (Pinkerton et al., 1985, J. Chem. Educ. 62:965).

The use of radiolabelled chelator conjugates may be preferable over the direct labeling systems for a number of reasons. First, the chelator may provide metal complexes of greater in vivo stability. A second advantage arises if a metabolically cleavable group is included in the linking portion of the bifunctional chelator to allow for rapid clearance and decreased accumulation of radiolabelled protein in non-targeted tissue. Lastly, direct labeling may require attachment of the radioisotope to functions of the protein which lower or otherwise interfere with the in vivo targeting of the peptide or protein.

A number of bifunctional chelating agents have been reported in the scientific literature. Tolman et al. (U.S. Pat. No. 4,732,864) have described the use of the cysteine rich, metal binding protein metal-lothionine and metalliothionine fragments conjugated to targeting molecules. However this method suffers from the fact that metallothionine is itself a large molecule and it may be difficult to purify and characterize such conjugates.

Schwartz et al. (1991, Bioconjugate Chem. 2:333) describe a series of bifunctional technetium chelators based on pyridyl hydrazines. This method of binding the radiometal is novel, however these chelators may not be useful for binding site specifically to antibodies or glycoproteins through the oxidized carbohydrate since the technetium binding hydrazide end may preferentially react with the aldehydes. Chemical solutions to this problem are not described.

Fritzberg et al. (EP 0188526; 1988, Proc. Natl. Acad. Sci. U.S.A. 85:4025) have described several examples of bifunctional dithiolate diamide technetium chelators. However, such methods for chelation of technetium are cumbersome since the compounds must be pre-chelated to technetium and then conjugated to antibodies. Also such compounds require a free thiol group for technetium chelation. Since free thiols are somewhat unstable to oxidation/dimerization and may reduce protein disulfide bonds if exposed to protein, the thiol functions in the chelator must be protected (masked) during final synthesis and then unprotected before technetium chelation. This is cumbersome.

Yokoyama et al. (U.S. Pat. No. 4,287,362; 1986, Int. J. Nucl. Med. Biol. 12:425; 1987, J. Nucl. Med. 28:1027) describe bifunctional chelators based on thiosemicarbazone derivatives of 1,2 dicarbonyl compounds. These compounds have a thiocarbonyl moiety as the technetium chelating group. Similar systems are described by Wu (EP 0306168) and are based on thiosemicarbazone derivatives of dicarbonyl compounds. Thiosemicarbazone derivatives, which are formed by a condensation reaction through removal of water, may be susceptible to hydrolysis. Such compounds can be expected to be easily hydrolyzed in acidic aqueous media, or possibly prematurely in vivo, leading to loss of metal-chelate complex integrity. These types of hydrazone chelators are different from the present invention.

It is therefore an object of the present invention to provide a novel class of sulfur containing chelators that overcome several of these disadvantages. It is a further object to provide for specific or non-specific conjugation to a targeting molecule.

It is another object of the invention to provide sulfur-containing metal chelators that do not contain free thiol groups, and that are free of potential undesirable side reactions with proteins or in vivo.

It is still another object of the present invention to provide sulfur-containing metal chelators that are chemically stable, and in particular that are resistant to oxidation and whose conjugates can be more resistant to hydrolysis.

Another object of the invention is to provide sulfur-containing metal chelators that contain, in some cases, in addition to a pair of thiocarbonyl chelating groups, still other pairs of chelating thiocarbonyl or carbonyl groups which may be useful for providing additional stability of radiometal chelates in vivo.

3. SUMMARY OF THE INVENTION

The present invention is directed to bifunctional chelating agents of the formula:

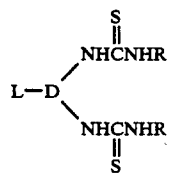

in which L is a linker, D is an alkyl, cyclic alkyl or aryl group having the NHCSNHR groups at the 1,2-, 1,3-, 1,4- or 1,5- (etc.) positions, and R is H or a substituent with the general formula:

in which
 a=0 or 1;
 b=0-10;
 Y=S, O or $H_2$;
 d=0-2;
 e=1-10; and
 Z=is H, $N+(R')_3$ $x^-$, $SO_3H$, $CO_2H$, OH, $H_2PO_3$; in which $X^-$ is a counterion such as a halide or an acid salt and R' is a $C_1$ to $C_4$ lower alkyl.

In one embodiment, D is a 1,2- or 1,3 substituted straight chain alkyl group. In a preferred embodiment D is a 1,2- or 1,3 substituted benzene ring. The invention further provides methods for preparing the bifunctional chelating agents by reacting diisothiocyanate groups with nucleophiles, particularly amines, hydrazides and thiosemicarbazides.

The compounds of this disclosure are based on a series of thiocarbonyl compounds which are functionally different from those described earlier. The systems contain no free thiols to interfere with protein disulfides, but rather contain a thiocarbonyl moiety derived from isothiocyanates which can serve as a sulfur donor for metal, e.g., technetium, chelation.

It has been discovered that diisothiocyanate derived thiocarbonyl containing compounds that include a linker are particularly useful chelating agents. The chelating agents of the invention are particularly advantageous for conjugating to targeting molecules, such as proteins, antibodies, peptides, nucleic acids, or steroids, in specific or non-specific attachment. Another advantage of the chelating agents is that they lack free thiols. Thus metal chelates can be formed after conjugation of the chelating agent to the targeting molecule. A further advantage of the chelating agents is their chemical stability, in particular their resistance to hydrolysis and to oxidation. The instant invention also provides, in some cases, the opportunity to prepare chelators that contain carbonyl or thiocarbonyl pairs to help chelate the metal ion, in addition to the isothiocyanate derived thiocarbonyl groups.

The chelating agents of the invention can be conjugated to various targeting molecules via the linker using well known linking methods. The targeting molecule-chelating agent conjugates can be complexed with metal ions, preferably radiometals, and used for therapy or in vivo or in vitro diagnosis of disease.

4. BRIEF DESCRIPTION OF THE DRAWINGS

FIG. 1 Autoradiogram of an instant thin layer chromatography (ITLC) plate developed with water. Tc-99m-GLUCOSCAN was applied on the left. Peptide conjugated with chelating agent A was incubated with Tc-GLUCOSCAN and applied on the right. The plate was eluted for 10 min.

Figure 2:
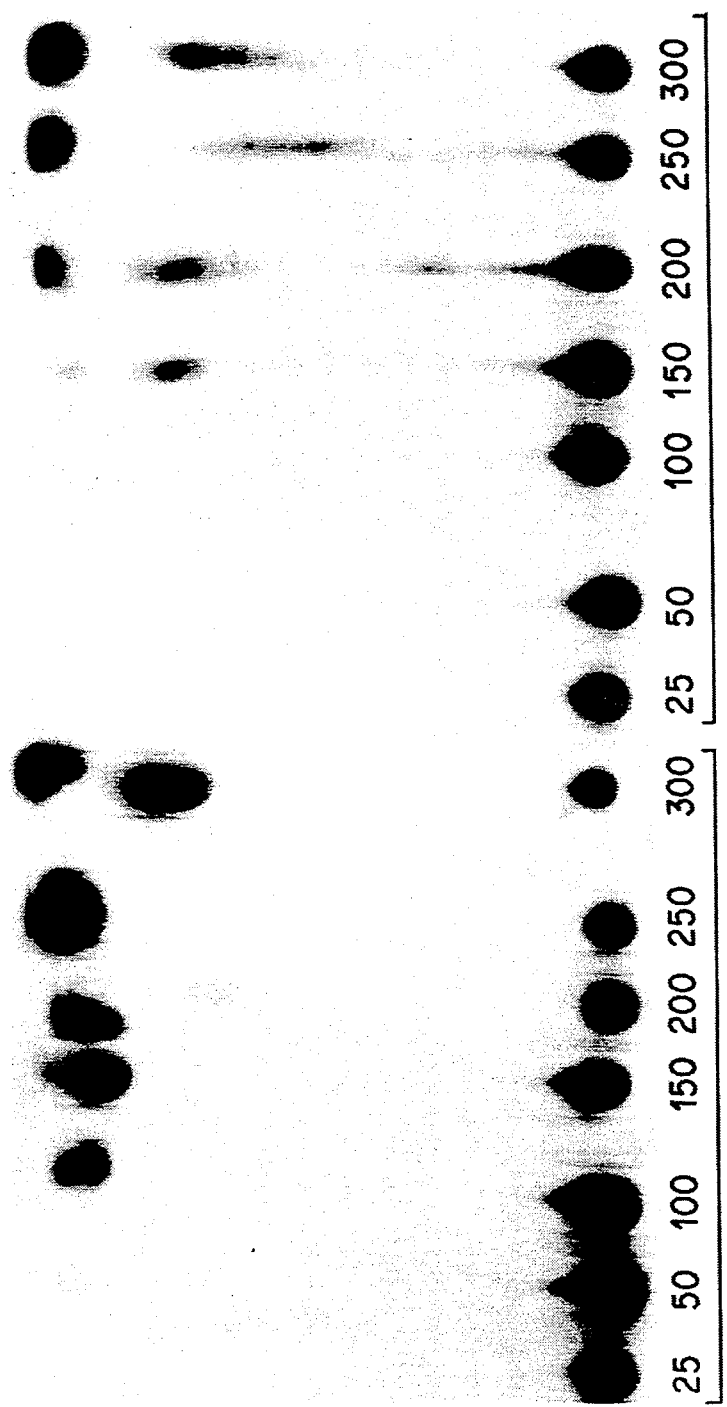
Figure 3A:
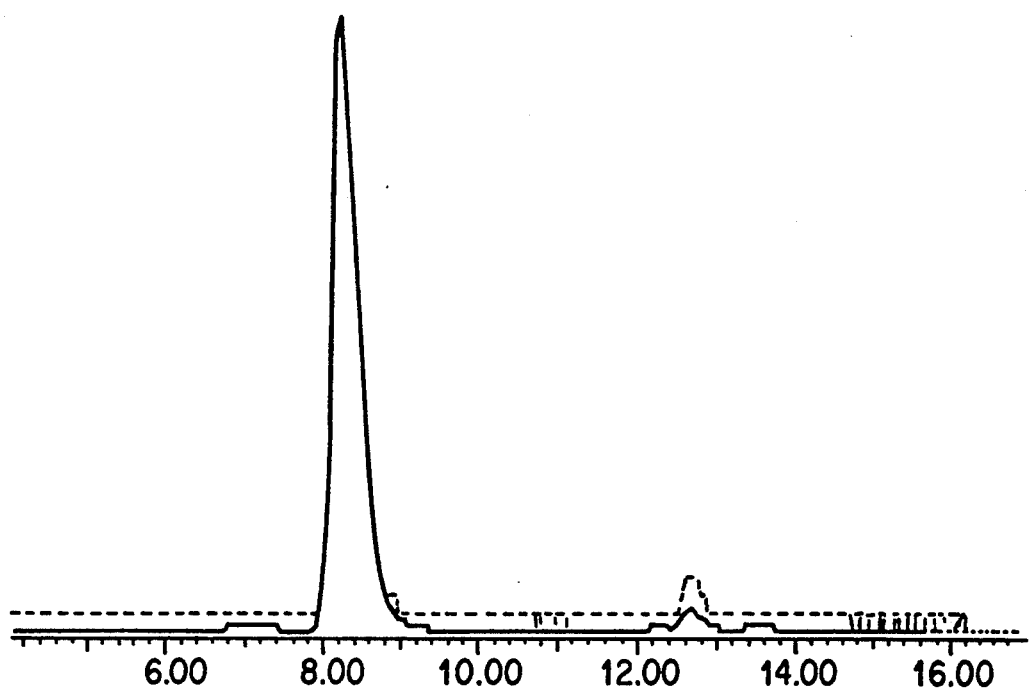
Figure 3B:
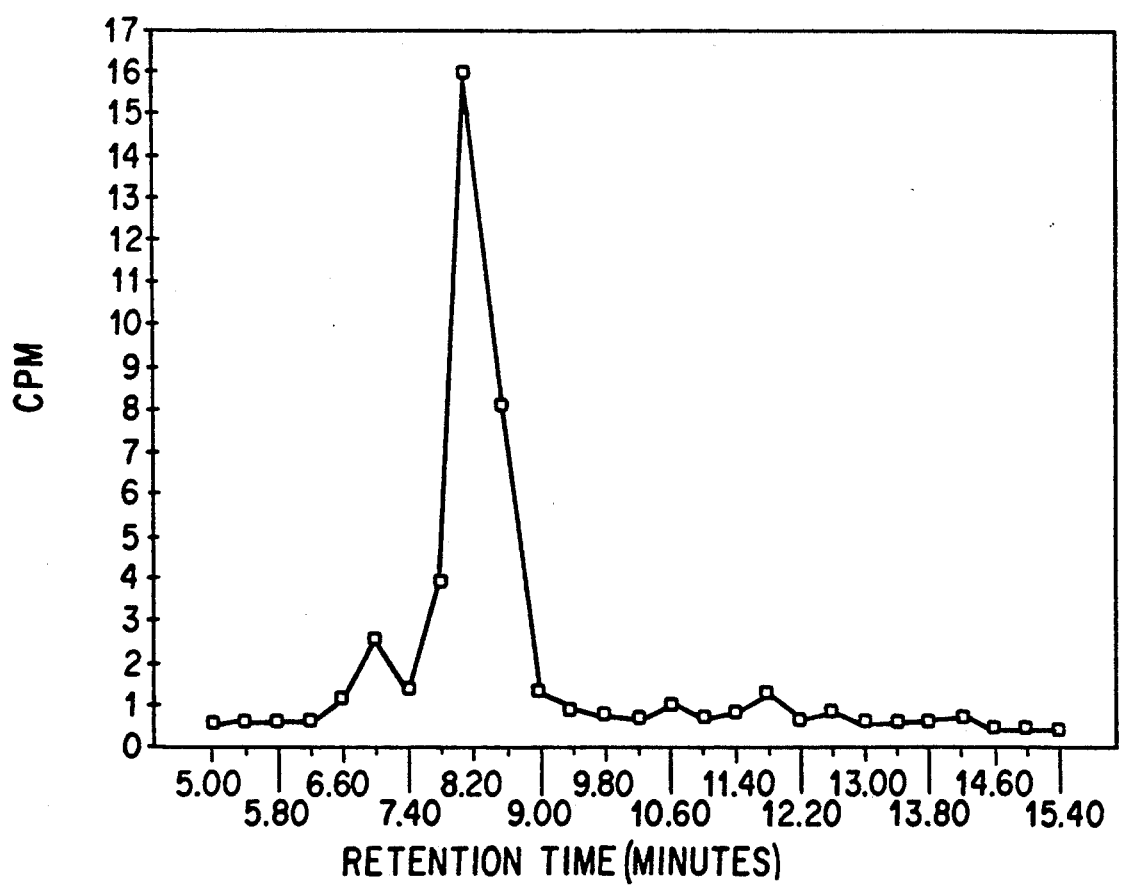
Figure 3C:
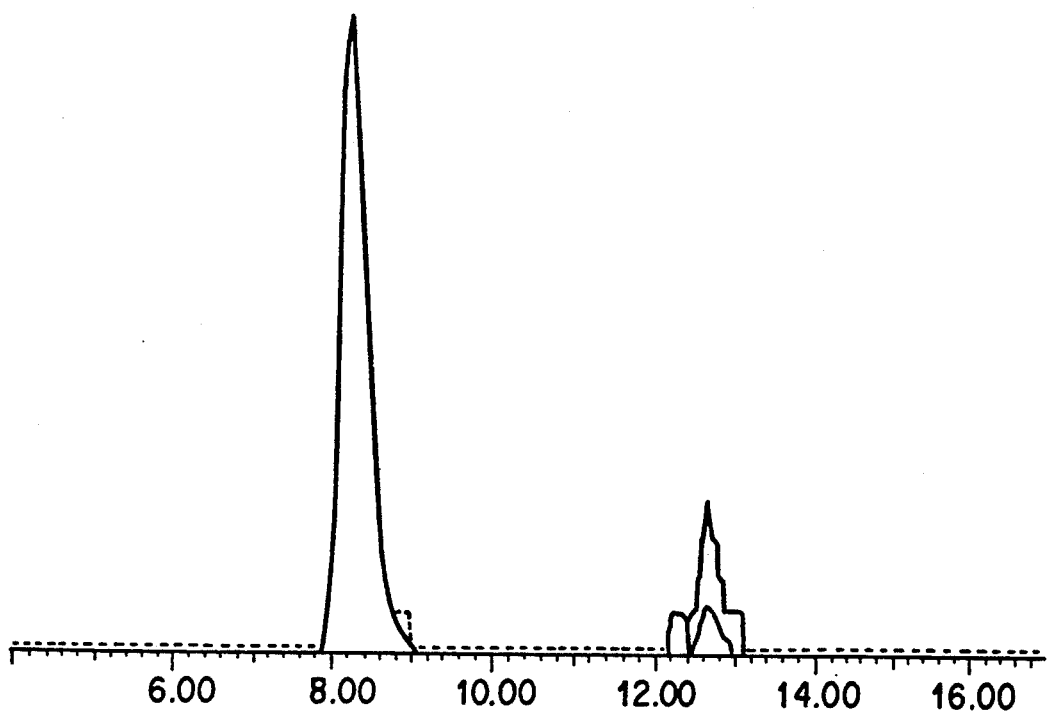
Figure 3D:
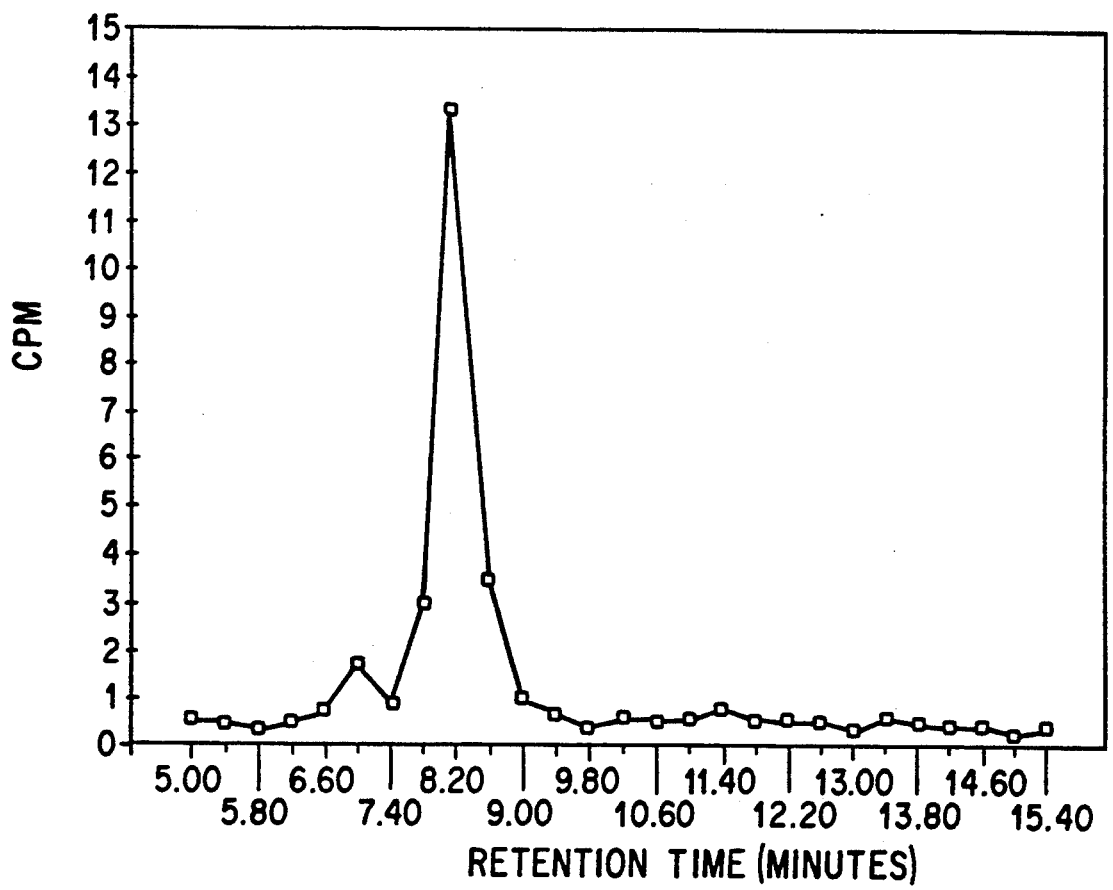
Figure 4A:
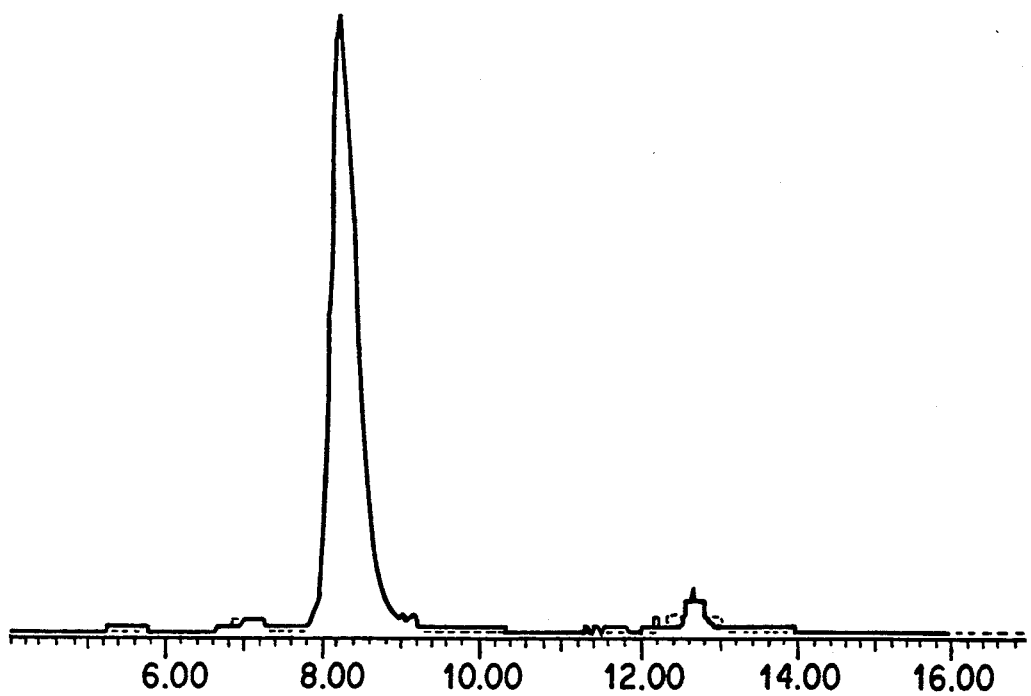
Figure 4B:
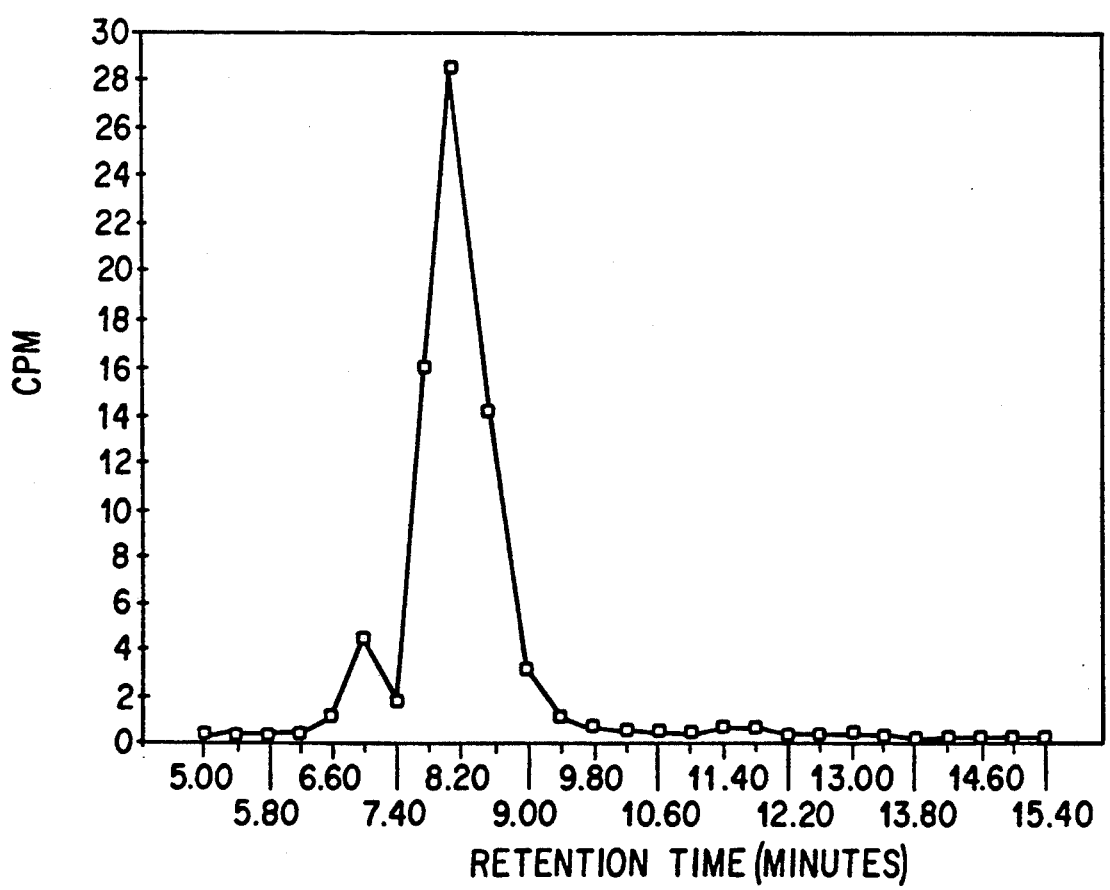
Figure 4C:
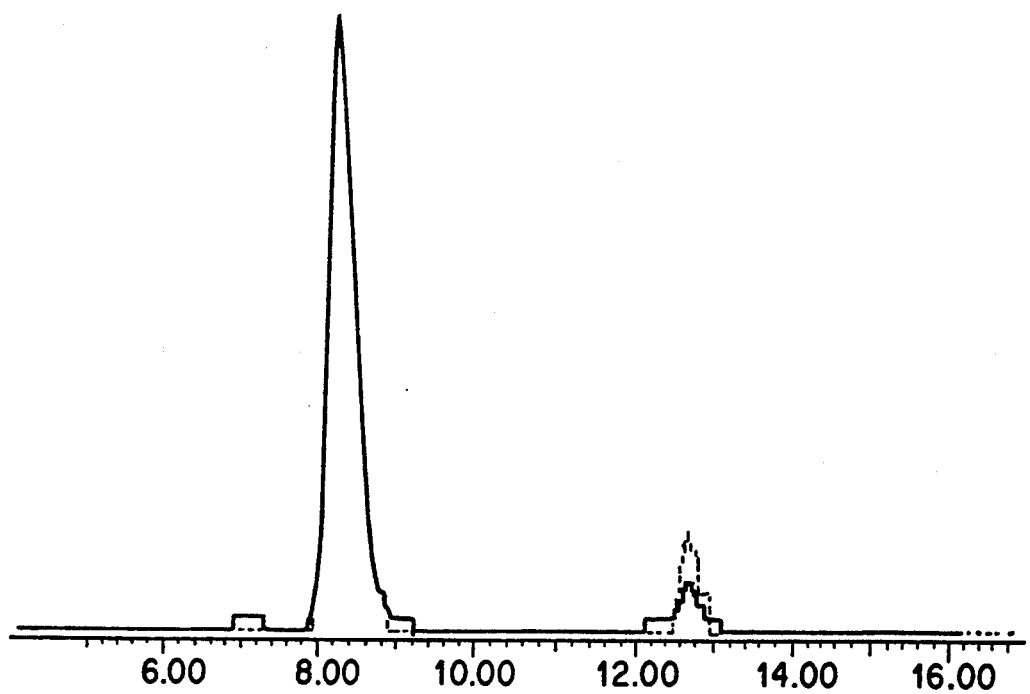
Figure 4D:
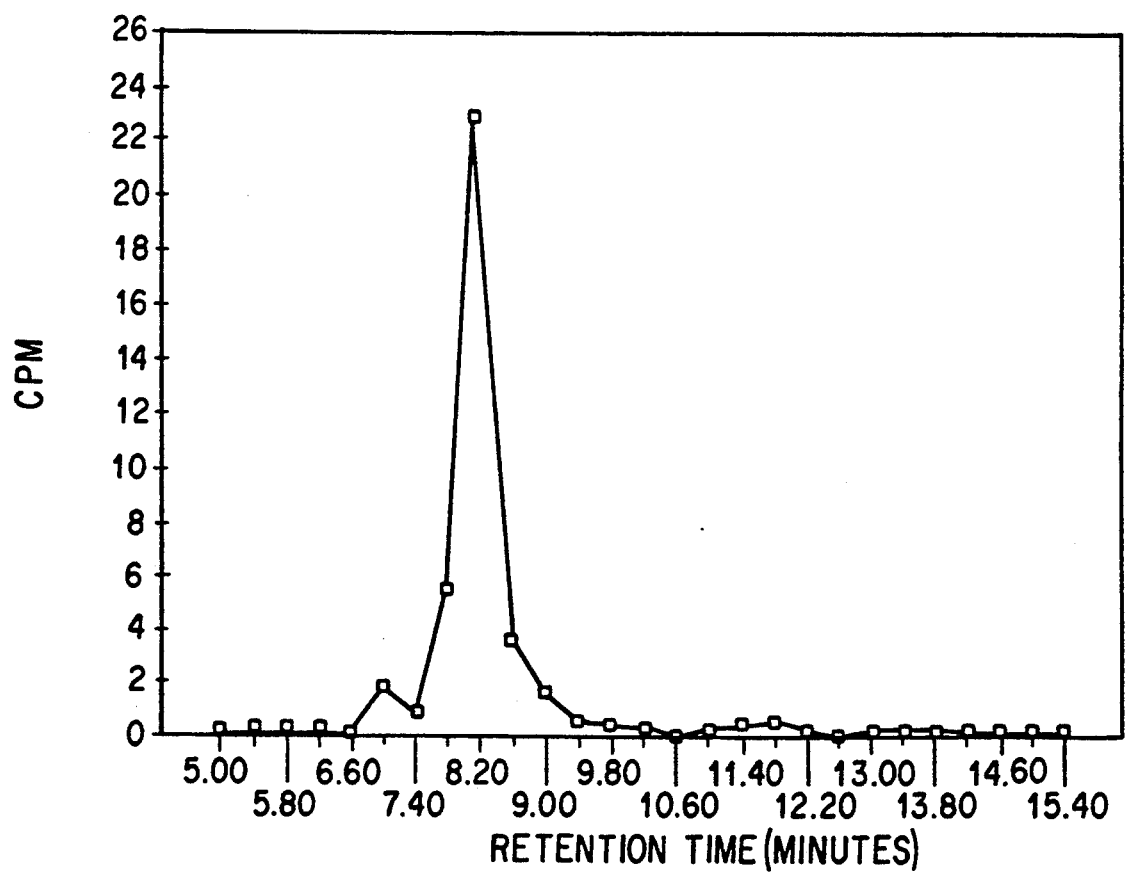
Figure 5A:
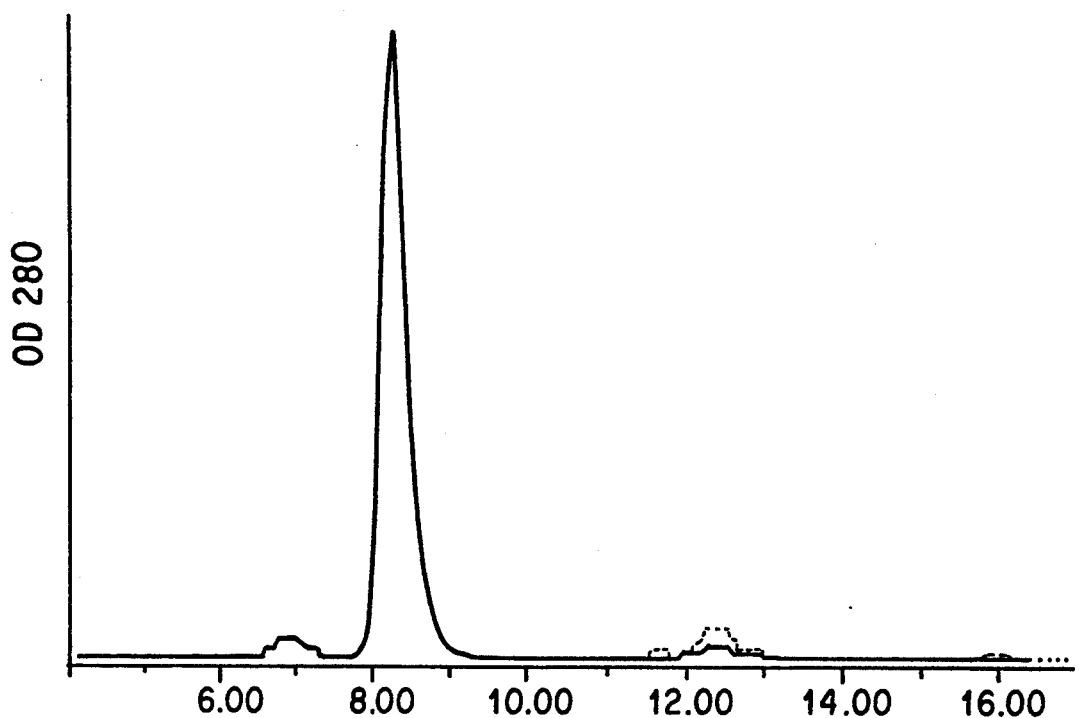
Figure 5B:
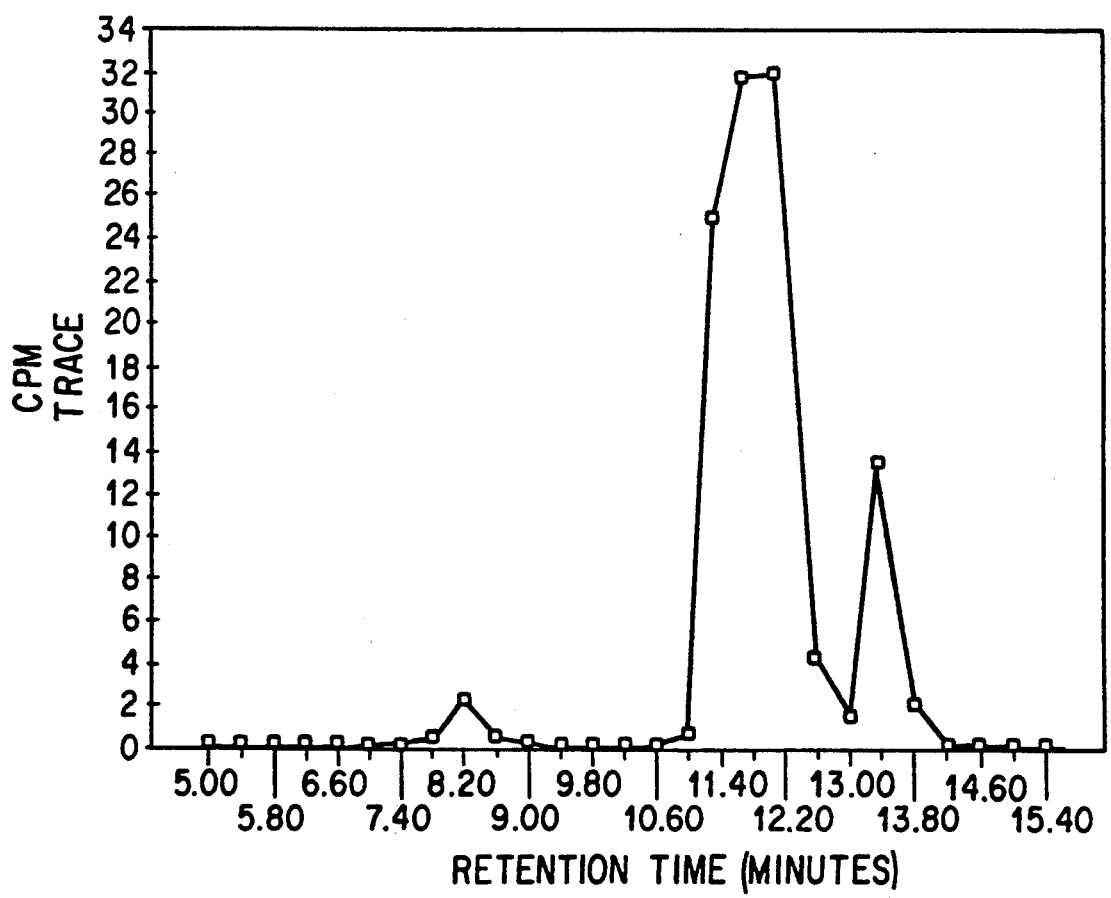
Figure 5C:
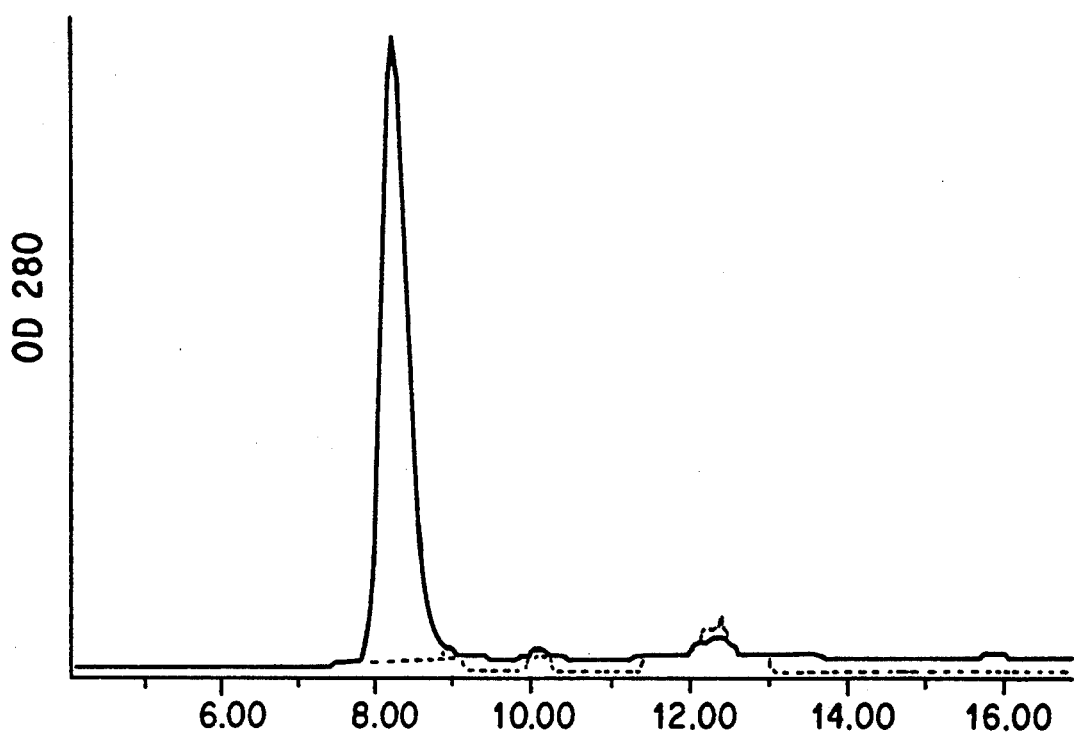
Figure 5D:
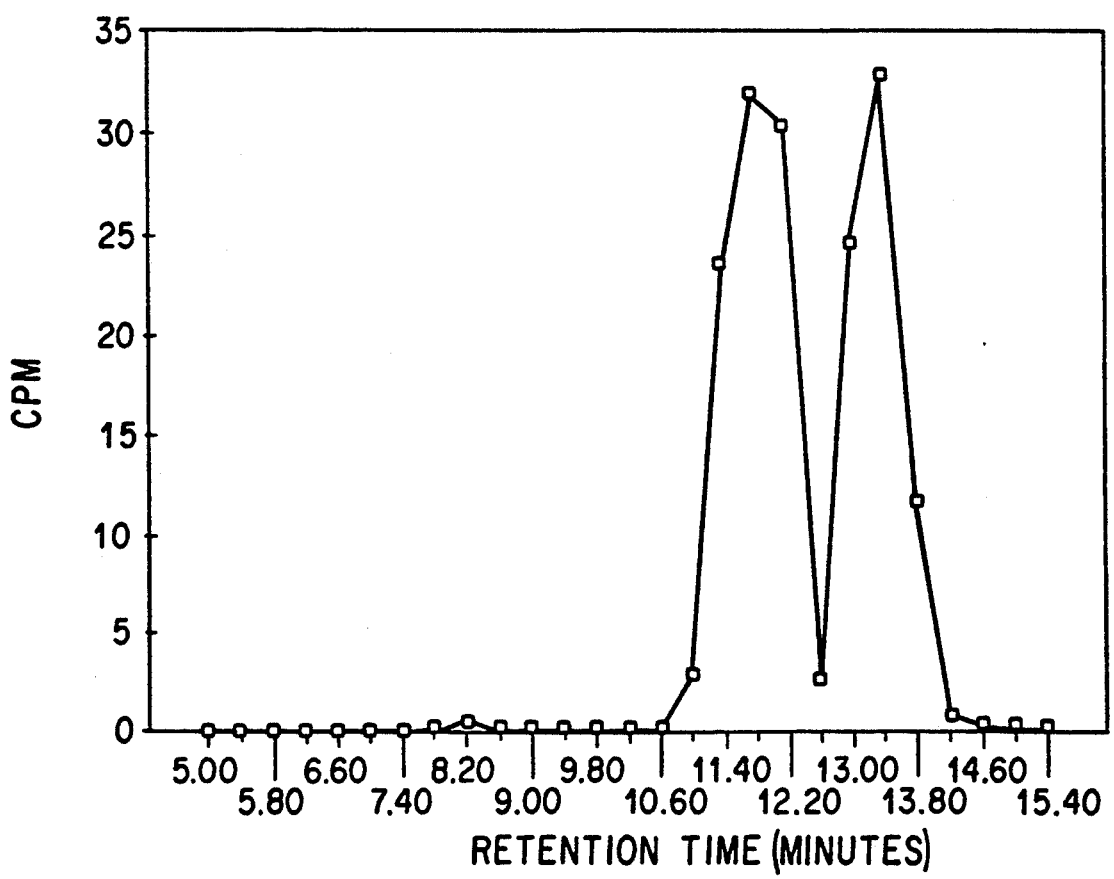

FIG. 2. Autoradiogram of an ITLC analysis of the chelating capacity of (a) chelating agent A-peptide conjugate and (b) chelating agent A alone. Samples are spotted to reflect μCi of Tc-99m per ng of conjugate.

FIG. 3. HPLC analysis of a chelating agent B-antibody conjugate labeled with Tc-99m. In this experiment, the ratio of chelating agent to aldehyde groups on the antibody was 1:1. HPLC analysis conditions are described in Section 10., infra. Panels (a) and (c): detection of OD at 280 nm. The antibody peak predominates. Panels (b) and (d): detection of Tc-99m (counts per minute (CPM)). Most of the radioactivity is detected in the antibody peak. Panels (a) and (b) were obtained from a sample of 1.48 mg/ml conjugate-Tc-99m complex; (c) and (d) were 0.74 mg/ml conjugate-Tc-99m complex.

FIG. 4. This HPLC analysis was performed generally as described for FIG. 3, with the exception that a 3:1 ratio of chelating agent B to aldehyde groups on the antibody was used. Panels (a) and (b): a 1.86 mg/ml sample; panels (c) and (d): a 0.93 mg/ml sample.

FIG. 5. Control HPLC analysis. In the first control assay, oxidized antibody (not - conjugated) was incubated with Tc-99m (panels (a) and (b)). In the second control assay, oxidized antibody was "reacted" with chelating agent A (which does not bind to aldehyde groups on oxidized antibody), and then incubated with Tc-99m (1.46 mg/ml sample, panels (c) and (d)). Elution of antibody is seen by OD at 280 nm (panels (a) and (c)). Radioactivity of Tc-99m is shown as cpm (panels (b) and (d)).

Figure 6:
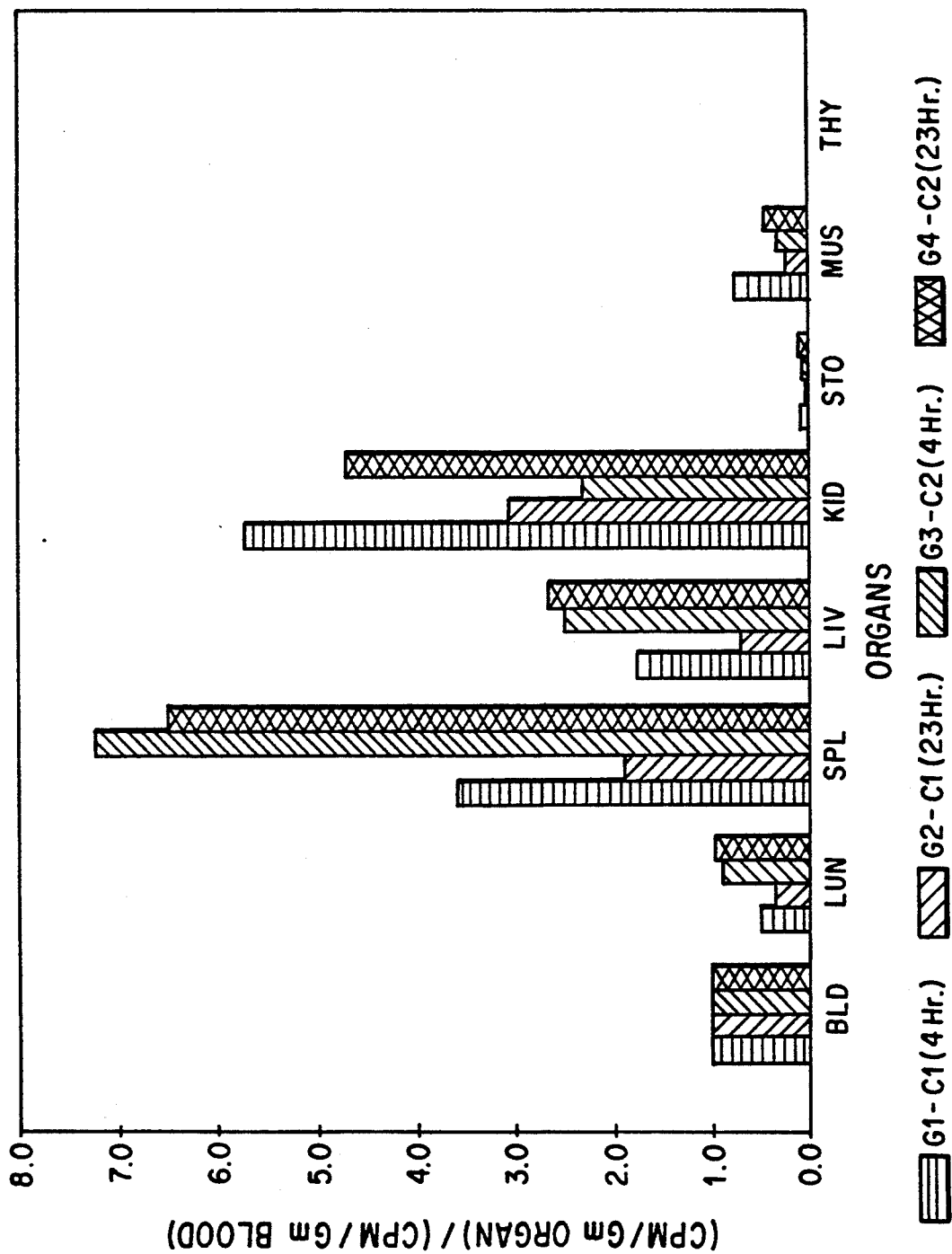

FIG. 6. Biodistribution of Tc-99m-labeled GLUCOSCAN and chelating agent A. The experiment is described in Section 11., infra. Abbreviations: BLB is blood; LUN is lung; SPL is spleen; LIV is liver; KID is kidney; STO is stomach; MUS is muscle; and THY is thymus. The results are shown as (CPM/gram of organ)/(CPM/gram of blood). Small cross-hatch: Tc-GLUCOSCAN distribution at an post injection; left-diagonal: Tc-GLUCOSCAN at 23 h; right-diagonal: Tc-chelating agent A at 4 h; large cross-hatch: Tc-chelating agent A at 23 h.

FIG. 7. Gamma camera tumor imaging of a mouse injected with Tc-99m-labeled anti-mammary tumor antibody B72.3 conjugated with chelating agent B. The images were obtained (a) three hours and (b) 20.5 hours after injection of the labeled conjugate. The tumor site is indicated in the photographs.

Figures 8A, 8B:

FIG. 8. Gamma camera blood clot imaging with Tc-99m-labeled SYRGDVRGDF-chelating agent A conjugate. The peptide conjugate localizes to a clot, indicated with an arrow in the Figure in the rabbit model. Images were obtained (a) 2 hours and (b) 4 hours after injection of the labeled conjugate.

5. DETAILED DESCRIPTION OF THE INVENTION

The present invention is directed to bifunctional diisothiocyanate derived thiocarbonyl-containing chelating agents that can be linked to targeting molecules. In particular, the derivatives have a thiourea (HNCSNH) functional group. As used herein, the term "bifunctional" refers to a compound that can be conjugated via a linking group to a targeting molecule (the first function) and that can chelate a metal (the second function). The thiourea-containing chelating agents, termed herein "chelating agents", are derived from diisothiocyanates. The chelating agents are of the formula:

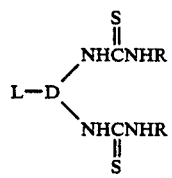

in which R is hydrogen (H) or a substituent with the general formula:

in which
a = 0 or 1;
b = 0–10;
Y = S, O or $H_2$;
d = 0–2;
e = 1–10; and
Z = is H, $N+(R')_3$ x -, $SO_3H$, $CO_2H$, OH, $H_2PO_3$; in which $X^-$ is a counterion such as a halide or an acid salt and R' is a $C_1$ to $C_4$ lower alkyl.

In a preferred embodiment, the chelating strength of the compounds may be augmented by the presence of additional carbonyl groups or thiocarbonyl groups at the R position. The compounds of the invention can be prepared so as to be highly water soluble (hydrophilic), or poorly water soluble (hydrophobic) by selection of an R group with the desired properties. As described in detail herein, the R group includes an alkyl group, a cyclic alkyl group, an aryl group, various carbonyl and thiocarbonyl functional groups, or various combinations thereof. The chelating agents of the instant invention are particularly useful for attachment (conjugation) to a targeting molecule to form targeting molecule-chelating agent conjugates, termed herein "conjugates". The compounds chelate metals, which can then be specifically targeted. As described herein, the targeting molecule-chelating agent-metal complex is useful in therapeutic treatment of a disease or disorder, or in in vivo or in vitro diagnosis. The thiocarbonyl compounds derived from diisothiocyanates and the preparations thereof are described in detail in Section 5.1., infra.

As used herein, the term chelating agent or chelator refers to a compound that binds a metal by multiple coordinate bonding between two or more electron-pair-donor groups of the chelating agent and the metal as an electron pair acceptor. According to the present invention, the sulfur atoms of the thiocarbonyl groups provide preferred coordination binding with electron pair acceptor metals.

Any metal capable of accepting election pairs from a chelating agent can bind the chelating agents of the invention. However, certain metals coordinate bond more strongly with sulfur containing substituents, and these metals are preferred. Preferably the metal is a radiometal, i.e., a radioactive isotope of a coordinate metal. Such metals are useful as imaging agents in diagnosis, and as therapeutic agents for targeted radiotherapy.

As used herein, the term "linker" refers to a group comprising a reactive group that is capable of reacting with a functional group on the target molecule to form a covalent bond between the chelating agent and the targeting molecule. The linker group can be chosen to provide specific attachment to the targeting molecule, i.e., bonding to a predictable site on the molecule or to provide non-specific attachment to the targeting molecule, i.e., bonding to one or more of sites on the molecule, which site or sites cannot be predicted. Linkers are described in detail in Section 5.2., infra.

As used herein, the term "targeting molecule" refers to a molecule that specifically interacts with a target. Examples of targeting molecules (and the target) are antibody (targeted to its antigen), protein (targeted to a receptor, as substrate, or a regulatory site, e.g., on a DNA (gene) or RNA sequence), peptide (targeted usually to a receptor), nucleic acid (targeted to a complementary nucleic acid, e.g., RNA or DNA), steroid (targeted to a steroid receptor), and the like. The invention is not limited by the choice of targeting molecule.

The bifunctional chelating agents conjugated to targeting molecules (conjugates) and complexed (via the chelating group) with metal ions can be useful in therapy of or in vivo or in vitro diagnosis of diseases. In a preferred embodiment, the conjugates or conjugate-metal complexes can be admixed with a pharmaceutically acceptable carrier or incipient for administration to a subject. Preferably the subject is an animal, more preferably a mammal, including but not limited to a dog, cat, mouse, rat, horse, cattle or other farm animal, and most preferably a human.

5.1. BIFUNCTIONAL DIISOTHIOCYNATE DERIVATIVES

The bifunctional diisothiocyanate derived thiocarbonyls of the invention are characterized by having in addition to a linking group capable of covalently binding to a targeting molecule (discussed further in Section 5.2. infra), diiosthiocyanate derived thiocarbonyl groups capable of coordinate binding with a metal. The diisothiocyanate derived thiocarbonyls are preferably thioureas and derivatives thereof. The compounds are preferably formed by reacting a 1,2-, 1,3- . 1,4- or 1,5- (etc.) diamine or diamine-analogs (as described infra) with thiophosgene to form diisothiocyanate. The diisothiocyanate compound is susceptible to nucleophilic attack, resulting in formation of thiocarbonyl groups derived from the diisothiocyanates.

5.1.1. DIISOTHIOCYNATES AND PREPARATION THEREOF

The diisothiocyanate starting material for preparing the compounds of the invention is preferably a 1,2-, 1,3-, 1,4- or 1,5- (etc.) diisothiocyanate, and more preferably a 1,2 or 1,3- diisothiocyanate. Because isothiocyanates can be readily prepared from diamines, a diamine, or reducible dinitro-substituted compound, is as useful for preparing a diisothiocyanate which can be used to synthesize chelating agents. Such compounds, diamines in particular, may be preferred starting materials because of greater chemical stability.

It is contemplated that the two isothiocyanate groups are substituents on an alkyl chain of 2 carbons or greater, a cyclic alkyl, an alkyl substituted with one or more heteroatoms, an aryl or heteroaromatic group. The alkyl or aryl group substituted with the diisothiocyanates is termed herein the "scaffold". The linking group is also a substituent of the scaffold. Depending on the nature of the scaffold, the linking group can be found at the same or a different position as one of the isothiocyanate or isothiocyanate derivative groups. Thus the scaffold joins the linking functional group to the chelator functional group. Various diisothiocyanate and linker substituted scaffolds are contemplated as within the scope of this invention, and are not limited by the specific examples provided herein. For example, and not by way of limitation, the diisothiocyanates can be found on 1,2-substituted ethane, 1,2-substituted propane, 1,3-substituted propane, 1,2-substituted butane, 1,3-substituted butane, 1,4-substituted butane, 1,2- to 1,5-substituted pentane (conceivably derived from lysine), and so on. The alkyl group can be a straight chain or a branched chain alkyl. In the straight or branched chain alkyl scaffold, L can be at the 1,2,3, . . . or n position, in which n is the number of C atoms in the alkyl group. The scaffold can also comprise a cyclic alkyl group, for example, and not by way of limitation, cyclopentane (substituted with 1,2- or 1,3- diisothiocyanate, and L at the 1-, 2-, or 3-position), cyclohexane (substituted with 1,2-, 1,3- or 1,4- diisothiocyanate, and L at the 1-, 2- or 3-position) and cycloheptane (substituted with 1,2-, 1,3- or 1,4- diisothiocyanate and L at the 1,2,3,4 or 5- position). As used herein, the term cyclic alkyl group includes substituted as well as unsubstituted cyclic alkyl groups, e.g., methyl substituted cyclic alkyl, ethyl substituted cyclic alkyl and the like, and cyclic alkyl groups containing or substituted with heteroatoms, e.g., pyrrolidine, piperidine, and the like. In another embodiment, the scaffold can comprise an aromatic or heteroaromatic ring. As used herein, the term "aryl" refers to a conjugated system of pi electrons, in which there are an $4m+2$ number of pi electrons (where m=an integer), with a minimum of six. Aryl groups (with a linker at position 1) include but are not limited to 2,3- 2,4- or 2,5-benzene, pyridine, furan, pyrole and the like. In specific embodiments, infra, the scaffold is a 1,2-substituted benzene and a 1,3-substituted benzene.

Diisothiocynates described above can be prepared by well known methods in the art (e.g., D'Angeli et al., 1963, J. Org. Chem. 28:1596–1600; Lieber and Slutkin, 1962, J. Org. Chem. 27:2214–2217; and Klöpping and van der Kerk, 1951, Rec. trav. chim. 70: 949–961). In a specific embodiment, diisothiocyanates can be prepared by reacting a diamine substituted scaffold group or an analogous compound with excess thiophosgene, with the proviso that the diamines not be in close enough proximity or on a flexible scaffold such that a cyclization reaction occurs. Such deleterious cyclization can occur by nucleophilic attack of an unreacted amine on neighboring isothiocyanate. Generally preparation of diisothiocynates are well known reactions. The specific reaction conditions will depend on the choice of diamine or diamine analog, e.g., as discussed below. Since the scaffold will also have a functional group that acts as or forms a linker, care must be taken to protect that functional group if it could itself undergo chemical conversion or interact with the isothiocyanate functional groups being prepared in the reaction. For example, if the linker group contains a free amine, the amine can be blocked with a protecting group such as tert-butoxycarbonyl group. The tert-butoxycarbonyl group can be removed subsequently by treatment with trifluoroacetic acid.

In a preferred embodiment, the scaffold comprises a benzene ring. When a 1,2-substituted benzene is used, a preferred starting material for reaction with thiophosgene is benzimidazole (e.g., 5-benzimidazole-carboxylic acid). The nitrogens of the imidazole ring are reactive with thiophosgene. If free amines in the 1,2 positions, rather than the imidazole ring, were reacted with thiophosgene, a significant if not dominant side reaction of nucleophilic attack by one amine at the isothiocyanate derivative of the other amine would probably occur. Thus, to avoid this cyclization reaction, the benzimidazole group is used. See, Hull, 1979, Synthetic Commun. 9:477–481. Thus, in a preferred embodiment, the chelating agent has the formula:

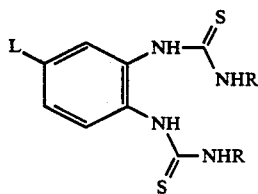

II in which R is defined as above.

In the situation in which a 1,3-substituted benzene is used, the free amines can be reacted with thiophosgene to give a 1,3-diisothiocyanatobenzene. Although the present invention is not limited to a particular mechanism, it is believed that the rigid structure of the benzene ring, which has little conformational freedom, and the distance between the amines in the 1,3-positions preclude reaction of one amine with the isothiocyanate derivative of the other amine, and allows both amines to react with thiophosgene. Thus, in another preferred embodiment, the chelating agent has the formula:

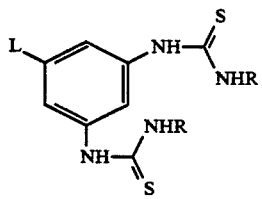

III in which R is defined as above.

5.1.2. REAGENTS FOR ADDITION TO THE DIISOTHIOCYANATES

The R group shown in Scheme I, supra, is added by nucleophilic attack at the isothiocyanate. Suitable reagents for nucleophilic attack of the isothiocyanate groups include but are not limited to amines. As used herein, the term amine refers to a primary or secondary alkylamine, cyclic alkylamine, or aryl amine. Also contemplated by the term amine are substituted alkyl amine, substituted cyclic alkyl amine, substituted aryl amine, amino acids, amines substituted with heteroatoms, and the like.

In a preferred embodiment, an acid hydrazide or semicarbazide group can be reacted with the isothiocyanate to yield a thiosemicarbazide derivative. In another embodiment, a thioacid hydrazide or thiosemicarbazide can be reacted. Thioacid hydrazide and thiosemicarbazide groups are termed herein "thio-analogs" of hydrazide and semicarbazide groups. Addition of thiocarbonyl- or carbonyl-containing groups is preferred since this increases the density of electron pair donors available to the metal for chelation. Thiocarbonyl groups are more preferred since addition of thioacid hydrazide or thiosemicarbazide to the diisothiocyanate will yield a chelating agent with four thiocarbonyl groups in close proximity for chelating a metal, i.e., locating more sulfur electron donor atoms in the metal coordination sphere. The hydrazides or semicarbazides, including the thio-analogs, for use in the invention can be substituted with alkyl, cyclic alkyl, or aryl groups, including substituted alkyl, substituted cyclic alkyl and substituted aryl groups, in which the substituents include but are not limited to heteroatoms.

The amine or hydrazide or semicarbazide (including thio-analogs thereof) group for addition to the isothiocyanate pair can have primarily hydrophobic character, e.g., by substitution with unsubstituted alkyl, cyclic alkyl, or aryl groups. In another embodiment, the amine or acid hydrazide or semicarbazide (including thio-analogs thereof) group for addition to the isothiocyanate pair can have primarily hydrophilic character, e.g., by substitution with a polar group such as, but not limited to, a quaternary amine salt, an acid or acid salt, a hydroxy group, and the like. Examples of polar substituents include but are not limited to trimethylammonium chloride, trimethylammonium acetate, trimethylammonium trifluoroacetate and the like; and acids such as sulfonic, phosphonic and carboxylic, including the sodium, potassium, lithium, calcium, and magnesium salts thereof. For example, in a preferred embodiment in which b=0 and d=0, R can have the following structure:

IV in which a is 1 or 2, e is 0–10, Y is $H_2$, S or O, and Z is a polar group as described above.

In specific embodiments, described in the examples, infra (carboxymethyl)trimethylammonium chloride hydrazide (Girard Reagent-T) and 4-methyl-3-thiosemicarbazide are reacted with the diisothiocyanate. These and other groups for use in the invention, including but not limited to acetic hydrazide, benzoic hydrazide, fluoresceinthiosemicarbazide, 4-2-(trimethylammonium) ethyl-3-thiosemicarbazide, and 4-sulfomethyl-3-thiosemicarbazide, can be obtained from commercial sources, e.g., Aldrich or Sigma, or alternatively can be synthesized via ordinary synthetic routes.

The reaction of the nucleophile, i.e., amine or hydrazide or semicarbazide (or thio-analogs thereof), with the di-isothiocyanate can be performed under fairly standard conditions. Generally, the di-isothiocyanate and the reactive nucleophile are dissolved in a polar inert solvent in which they are soluble. Examples of such solvents are acetonitrile, dimethylformamide, dioxane, water, alcohols or mixtures thereof. Generally the reaction can be run at room temperature, although where a difficult nucleophilic addition to the isothiocyanate is contemplated, e.g., with a secondary amine, temperature can be increased. The nucleophile should be added at greater than a two-fold molar excess over the diisothiocyanate to ensure quantitative di-addition.

5.1.3. REACTION OF DIAMINES WITH ISOTHIOCYANATE DERIVATIVES

It will be readily appreciated by one of ordinary skill in the art that the reverse reaction of nucleophilic attack at a diisothiocyanate compound can be used to yield the thiourea derivatives of the instant invention. For example, isothiocyanate derivatives of the general formula:

SCNR"

in which R" is hydrogen or a substituent of the general formula for R, supra, can be reacted with diamines, as described in Section 5.1.1., supra to form thiourea derivatives.

5.2. LINKER GROUPS

The linker groups, also termed herein "linker", for use in the compounds of the invention are suitable for conjugating the chelating agent to a targeting molecule. In another embodiment, the linker groups can be used to conjugate the chelating agent to a solid support. In particular, the linker groups are reactive with functional groups on proteins, especially antibodies or antibody fragments, peptides, nucleic acids, steroids, and other targeting molecules of interest. The reactive group of the linker can be spaced from the scaffold via an alkyl (including saturated and unsaturated) group, a cyclic alkyl group, a substituted alkyl or cyclic alkyl group, or an equivalent spacer group, including a peptide sequence. In a specific embodiment, the linker reactive group is spaced from 0 to about 20 atoms from the scaffold although spaces of more than 20 atoms are also contemplated.

In a specific embodiment, the linker comprises a cleavable linker as disclosed in U.S. Pat. No. 4,671,958, which is specifically incorporated herein by reference in its entirety.

The linker or a functional group useful to form the linker, termed herein a "linker precursor" may be present on the scaffold prior to derivitization of the diisothiocyanate group by nucleophilic addition. In the event that the linker or linker precursor is reactive at some step in the preparation of the isothiocyanate derivatives, the linker or linker precursor should be protected. For example, if the linker is an amine, the amine should be protected prior to reaction with thiophosgene so as not to form a different and competing isothiocyanate. A suitable protecting group is tert-butoxycarbonyl.

Alternatively, a linker can be added or modified after derivitization of the diisothiocyanate. Since the diisothiocyanate derivatives are fairly non-reactive, this strategy may be preferred. In a specific example, infra, a carboxylic acid linker or linker precursor is modified to become a hydrazide linker. Various modifications of linkers and strategies therefore are well known in the art, and are within the scope of the present invention.

5.2.1. ATTACHMENT TO OXIDIZED CARBOHYDRATE MOIETIES

Glycoproteins are biologically important macromolecules which share structural characteristics, in particular carbohydrate residues covalently attached to a polypeptide backbone. Since antibodies are glycoproteins, compounds may be attached to the carbohydrate moiety of the molecule. The carbohydrate moiety of the Fc region of an immunoglobulin may be utilized. Alternatively, the Fab or Fab' fragments of any immunoglobulins which contain carbohydrate moieties may be utilized in the reaction described herein. An example of such an immunoglobulin is the human IgM sequenced by Putnam, et al. (1973, Science 182:287).

As explained in detail below, the carbohydrate side chains of glycoproteins, in particular antibodies or Fab or Fab' fragments, may be selectively oxidized to generate aldehydes. The resulting aldehydes may then be reacted with amine groups (e.g., ammonia derivatives such as a primary amine, hydroxylamine, hydrazide, hydrazide, thiohydrazide, phenylhydrazine, semicarbazide or thiosemicarbazide) to form a Schiff base or reduced Schiff base (e.g., imine, oxime, hydrazone, phenylhydrazone, semicarbazone or thiosemicarbazone, or reduced forms thereof).

Cleavable linkers are desirable where more rapid clearance of the chelating agent-metal complex is desired. In the case where the linker comprises a cleavable peptide substrate, linker is modified by attaching a hydrazide or hydrazide derivative reactive group to one end of the cleavable peptide substrate linker. For instance, the peptide substrate linker attached to a scaffold, e.g., via an ester or amide link is further modified by attaching a hydrazide (e.g., glutamyl γ-hydrazide) to the opposite amino terminus of the peptide chain.

These hydrazide derivatives of the peptide linkers which are attached to a chelating agent, e.g., via an ester or amide link or a carbon-carbon bond, are then reacted with an oxidized glycoprotein, for example an immunoglobulin or immunoglobulin fragment, containing an oxidized carbohydrate. This results in hydrazone formation and the covalent attachment of the compound to the carbohydrate side chain of the glycoprotein via a linker group.

Oxidation of the carbohydrate portion or moiety of antibody molecules leads to formation of aldehyde groups. A variety of chemical oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, Organic Reactions 2:341; Bunton 1965, *Oxidation in Organic Chemistry*, Vol. 1 (Wiberg, ed.), Academic Press, New York, p. 367.

Oxidation of glycoproteins with these oxidizing agents can be carried out by known methods. In the oxidation, the glycoprotein is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0,001 to 10 mM and preferably 1.0 to 10 mM. The amount of the oxygen acid or salt thereof depends on the kind of antibody, but generally it is used in excess, for example, twice to ten times as much as the amount of the oxidizable carbohydrate. The optimal amount, however, can be determined by routine experimentation.

In the process for oxidizing glycoproteins with oxygen acids or salts thereof, the optional ranges include a pH of from about 4 to 8, a temperature of from 0° to 37°

C., and a reaction period of from about 15 minutes to 12 hours.

During the oxidation of the glycoprotein with an oxygen acid or a salt thereof, light is preferably excluded to prevent over-oxidation of the glycoprotein.

Alternatively, the carbohydrate moiety of the glycoprotein can be modified by enzymatic techniques so as to enable attachment to or reaction with other chemical groups. One example of such an enzyme is galactose oxidase, which oxidizes galactose in the presence of oxygen to form an aidehyde.

Oxidation of the carbohydrate portion of molecules with the enzyme, galactose oxidase has been described (Cooper, et al., 1959, J. Biol. Chem. 234:445-448). The glycoprotein is used in aqueous solution, the concentration being generally 0.5 to 20 mg/ml. The enzyme generally is used at about 5 to 100 units per ml of solution, at a pH ranging from about 5.5 to about 8.0. The influence of pH, substrate concentration, buffers and buffer concentrations on enzyme reaction are reported in Cooper, et al., supra.

Examples of conjugation of ligands to oxidized antibodies are provided in U.S. Pat. No. 4,741,900, which is specifically incorporated herein by reference in its entirety.

5.2.2. ATTACHMENT TO SULFHYDRYL GROUPS

Free sulfhydryl groups can be generated from the disulfide bonds of a protein or peptide that contains one or more disulfides, for example an immunoglobulin molecule. This is accomplished by mild reduction of the protein molecule. Mild reduction conditions are preferred so that the secondary and tertiary structure of the protein is not significantly altered so as to interfere with the protein function. Excessive reduction could result in denaturation of the protein. Of particular interest are immunoglobulin proteins. The disulfide bonds of IgG which are generally most susceptible to reduction are those that link the two heavy chains. The disulfide bonds located near the antigen binding region of the antibody molecule remain relatively unaffected. Such reduction results in the loss of ability to fix complement but does not interfere with antibody-antigen binding ability (Karush, et al., 1979, Biochem. 18:2226-2232). The free sulfhydryl groups generated in the intra-heavy chain region can then react with reactive groups of a compatible chelator to form a covalent bond which does not interfere with the antigen binding site of the immunoglobulin. Such reactive groups include, but are not limited to, disulfides that can react with a free thiol via disulfide transfer, e.g., pyridyl disulfide, p-mercuribenzoate groups and groups capable of Michael-type addition reactions (including, for example, maleimides and groups of the type described in Mitra and Lawton, 1979, J. Amer. Chem. Soc. 101:3097-3110).

Details of the conditions, methods and materials suitable for mild reduction of antibodies and antibody fragments as described generally herein, may be found in Stanwoth and Turner, in Handbook of Experimental Immunology, Vol. 1, Second Edition, Weir (ed.), Chapter 10, Blackwell Scientific Publications, London, 1973, which chapter is incorporated herein by reference.

Protein-chelator conjugates (or protein-metal ion complexes when pre-chelated metal ion is attached to the chelator prior to reaction of the chelator with protein), which are produced by attaching a compatible chelator with free sulfhydryl group of a reduced protein, for example a reduced immunoglobulin or reduced antibody fragment, do not activate complement. Thus, complexes of the conjugates may advantageously be used in in vivo imaging systems where release of the metal ion is not desirable.

The Fab' fragments of IgG immunoglobulins are obtained by cleaving the antibody molecule with pepsin (resulting in a bivalent fragment, F(ab')hd 2) or with papain (resulting in 2 univalent fragments, 2 Fab). The Fab and F(ab')$_2$ fragments are smaller than a whole antibody molecule and, therefore, permeate the target site or tissue more easily. This offers a distinct advantage for in vivo imaging since conjugates will more readily penetrate in vivo sites (e.g., tumor masses, infection sites, etc.).

An advantage is obtained when using conjugates formed with antibody fragments because these fragments do not cross a placental barrier. As a result, using this embodiment of the invention an in vivo site (such as a tumor) may be imaged in a pregnant female without exposing the fetus to the imaging compound, e.g., a radiometal.

Although attachment of a compound to sulfhydryl groups of an antibody molecule destroys complement fixation ability, such methods of attachment may be used to make antibody conjugates for use in the complement mediated release system as described in U.S. Pat. No. 4,671,958. In such an embodiment, a compound joined to a complement sensitive substrate linker can be attached to sulfhydryls of reduced Ig molecules or antibody fragments and delivered to the target in a mixture with intact antibody molecules that are capable of activating complement. The latter would activate complement which would cleave the compound from the former. The use of antibody fragments as carrier molecules in the complement mediated release system would permit the treatment of pregnant females, and offers the advantage of more rapid penetration of the conjugate into target sites.

According to the present invention, for attachment to sulfhydryl groups of reduced proteins, the substrate linkers are preferably modified by attaching an maleimide or disulfide group to one end of the linker. The unmodified site on the linker is covalently attached to the scaffold of the chelating agent. For instance, the substrate linkers which are ester or amide linked to compounds as described (Partis et al., 1983, J. Pro Chem. 2: 263; Means and Feeney, 1990 Bioconjugate Chem. 1:2-12).

As mentioned previously the linker may be one that is susceptible or resistant to cleavage by activated complement, or serum proteases.

When the maleimide or disulfide derivatives of the linker group are reacted with reduced protein or reduced protein fragments, including peptides, the linker group becomes covalently attached to the protein or fragment.

5.2.3. ATTACHMENT TO AMINO OR CARBOXY GROUPS OF A PROTEIN

A modification of conventional methods for linking compounds to proteins or peptides may also be used for the purposes of the present invention. These conventional methods attach compounds to amino or carboxy groups of the protein or peptide. A disadvantage of conventional methods is a decreased binding affinity of the protein for its target, e.g., antibody molecule for antigen (i.e., a decreased immunospecific activity) because of non-specific binding of the linkers to the antigen binding region of the antibody molecule. Thus, in order to utilize conventional linking methods, the substrate linker should be directed to a more optimal position on the protein, e.g., on the antibody molecule to allow immune complex formation and cleavage by complement. To this end, the antigen-binding arms (Fab regions) of the immunoglobulin or half-molecules are protected while either the amino or carboxy groups of the Fc region are reacted with a substrate linker, for example, via a soluble carbodiimide reaction. Any reactive groups in the chelating agent that could interfere with binding of linker to the protein should be blocked before reacting the protein with the linker.

Specific groups for attachment to a reactive amine (an $\alpha$-amine or more likely $\epsilon$-amine, e.g., of lysine) include carboxylic acid, a carboxylic acid ester, e.g., methyl ester, isothiocyanate, succinate, and the like. Specific groups of attachment to carboxylic acid (e.g., aspartic acid or glutamic acid) include amines, hydrazines, hydrazides, semicarbizides, and the like. Binding of amines with carboxylic acids are preferably mediated by a carbodimide-mediated condensation.

5.2.4. LINKERS FOR CONJUGATION WITH NON-PROTEIN TARGETING MOLECULES AND SUPPORTS

Generally the same strategies described above for conjugation with oxidized aldehyde groups or with free amino groups can be used to conjugate chelating agents of the invention to other targeting molecules. For example, oxidation of a ribose or deoxyribose of a nucleic acid sequence can provide an aldehyde for reaction with linkers described in Section 5.2.1, supra. Similarly, steroids or other targeting molecules can be prepared with a reactive aldehyde functionality. Steroids or other targeting molecules may naturally have an aldehyde that is reactive.

In another embodiment, targeting molecules can be prepared with amino groups that react with the linkers described in Section 5.2.3, supra. It is even possible to prepare targeting molecules with a reactive thiol, which is capable of reacting with linker groups such as are described in Section 5.2.2, supra.

Moreover, as known to one of ordinary skill in the art, similar reactive groups can be found on or prepared on solid supports, e.g., sephadex, sepharose, cyanogen bromide activated sepharose, carboxymethyl cellulose, agarose, and the like.

5.3. PREPARATION OF COMPLEXES

Chelating agent-metal ion complexes can be prepared by bonding the metal ion directly to the chelator. Conventional methods of attaching metal ions to chelators may be utilized to accomplish binding. Generally, reduced pertechnetate (technecium thought to be in the form of TC(III), Tc(IV) or Tc(V), or any combination thereof), reduced perrhenate (rhenium thought to be in the form of Re(III), Re(IV), or Re(V), or any combination thereof), copper (generally Cu(II), although Cu(I) and Cu(III) are also possible), mercury (Hg(I) or Hg(II), or both) or lead (Pb(II) or Pb(IV), usually) are preferred metal ions for chelation with the chelating agents of the invention. Examples of radiometals for chelation are technetium-99m (Tc-99m), rhenium-186 (Re-186), and -188 (Re-188), copper 67 (Cu-67), silver 111 (Ag-111), mercury 197 (Hg-197), lead 212 (Pb-212) and bismuth 212 (Bi-212). Bi-212 is the decay product of Pb-212. With a half-life of about 10.6 hours, Pb-212 rapidly decays to Bi-212, which in turn rapidly decays (half-life of about 1 hour) with emission of an alpha particle. Other metal ions, such as indium (particularly In-III) and the lanthinide ions (generally Ln(III), and in particularly gadolinium Gd(III)) cannot be excluded. Other metal ions used in vivo diagnostics are discussed in Section 5.4.2., infra.

Preferably the chelating agent will be conjugated to the targeting molecule, e.g., antibody or peptide, prior to chelation with the metal. Conjugation to the target molecule prior to chelation is advantageous because the sulfur atom electron pair donors are present as thiocarbonyls rather than thiols, and are therefore non-reactive, e.g., with disulfides or free sulfhydryls in a protein, especially an immunoglobulin. Another advantage of the instant chelating agents is their stability, so a targeting molecule-chelating agent conjugate can be stored prior to chelation with a metal ion. The ability to store the conjugates makes large scale production and distribution possible, and allows for lot-to-lot uniformity analysis and quality control.

Technecium labelling of the chelator is effected by conventional procedures. In a preferred embodiment, reduced Tc-99m is added to the conjugate as Tc-99m-Glucoscan (NEN Medical Products, North Billerica, Mass.), using established methods (e.g., Dswanjee, 1990, Seminar in Nuclear Medicine 20:5–27).

In another embodiment, pertechnetate can be obtained from commercial sources, usually as $NaTcO_4$ in ionic aqueous solution. Other forms of pertechnetate can be used, with appropriate modification of the chelating procedure. Reduction of the pertechnetate can be accomplished with a variety of reducing agents, for example, stannous ion, dithionite, borohydride, ferrous ion, and the like, in aqueous or aqueous-organic solution, buffered at about PH 4 to about PH 7. The reducing agent, preferably stannous ion, should be added in excess to ensure complete reduction of the pertechnetate. Reduction is normally effected under an inert gas atmosphere, e.g., nitrogen or argon, at about room temperature. The reduced pertechnetate is then reacted with the chelating agent, or more preferably the conjugate, and allowed to chelate. Unchelated technetium can be removed from the conjugate by simple techniques, e.g., gel filtration chromatography, membrane filtration, reverse phase chromatography, or ion exchange chromatography, depending on the molecular weight, hydrophobic, and ionic characteristics of the conjugate. Alternatively, when chelation is with the chelating agent alone, a scavenger for unreacted reduced pertechnetate can be added to prevent further reaction.

Rhenium labelling can be effected in substantially the same way as technetium labeling. With rhenium, however, special care must be taken to exclude oxygen from the system.

Copper labeling can be effected by reacting the conjugate or chelating agent with a solution of a copper ion salt, usually Cu(III) ions with counterions such as chloride, citrate, tartate and the like. Similarly, mercuric or lead salts, or mercury or lead in a form readily convertible to a salt, can be chelated in a manner analogous to Cu-67. Presently $^{67}CuCl_2$, $^{197}HgCl_2$, and $^{197}Hg(NO_3)_2$ are available on contract order from radioisotope suppliers. For example Oak Ridge National Laboratories can supply these compounds. Bismuth-212 is usually obtained from decay of lead-212. Thus a conjugate-lead-212 complex is allowed to decay to form the conjugate-bismuth-212 complex.

5.4. USES OF TARGETING MOLECULE-CHELATING AGENT - METAL ION -COMPLEXES

The targeting molecule metal ion complexes of the invention are useful in a variety of therapeutic and in vitro and in vivo diagnostic applications.

Throughout this application the term "cellular disorder" is meant to include all neoplasms, including cancers, adenomas, and hyperplasias; certain immunological disorders, including autoimmune diseases, transplantation diseases (e.g., graft-versus-host disease after bone marrow transplantation, or transplantation rejection), immune suppressive diseases, e.g., after kidney or bone marrow transplantation. Treatment of such cellular disorders involving, for example, bone marrow transplantation, may include purging (by killing) undesired cells, e.g., malignant cells or mature T lymphocytes.

In one preferred embodiment, the targeting molecule is an antibody conjugated with a chelating agent of the invention for use in imaging tumors. In specific embodiments, the antibody may be reactive with a tumor cell, preferably a human tumor cell. For example the antibody can be a monoclonol antibody reactive with human mammary tumor cells (Colchen et al., 1981, Proc. Natl. Acad. Sci. U.S.A. 78:3199-3203), e.g. monoclonal antibody B72.3, as shown in an example, infra. In another embodiment the antibody can be a monoclonal antibody specific for a marker for prostatic cancer (Horoszewicz et al., 1987, Cancer Res. 7: 927-936), e.g., monoclonal antibody 7E11. In yet a further embodiment, the antibody can be a monoclonal antibody specific for a colorectal cancer antigen, e.g., monoclonal antibody C46 (Granowska et al., 1989, Int. J. Colorect. Dis. 4: 97-108). The foregoing are provided as specific examples of antibodies for use as targeting agents and the invention is not limited to those examples. Other antibody targeting agents are known in the art and can be used with the chelating agents of the invention.

In another embodiment, the targeting molecule is a peptide useful for imaging thrombotic clots. In a specific example, infra, a peptide of the amino acid sequence SYRGDVRGDF-NH$_2$ is used. However, the chelators of the instant invention are not limited to use with this peptide, as they can be used with many peptides for imaging or therapy.

5.4.1. IN VIVO THERAPEUTICS

Therapeutic applications center generally on treatment of various cellular disorders, including those broadly described above, by administering an effective amount of the targeting-metal ion complexes of the invention. The properties of the molecule in being specific for and reactive with a particular target render it ideally suited for delivering metal ions to specific cells, tissues, organs or any other site having that particular antigen. The metal ions will generally be radiometals. Preferably the radiometals are rhenium-186 or lead-212 (bismuth-212), both of which have high energy decay.

Of particular use in this respect are antibodies, including polyclonal and monoclonal antibodies, and F(ab)$_2$ and Fab' fragments thereof. Antibodies are immunospecific for a unique target, termed an antigen. The binding affinity of antibody for antigen is usually very high; similarly, cross reactivity with other antigens is usually low. Thus antibodies are particularly suited to deliver a chelated metal ion to a target antigen and limit exposure of peripheral tissues that lack the target antigen to the effects of the metal ion.

In another embodiment, the targeting molecule is a peptide ligand of a receptor. Like antibodies, peptide ligands are highly specific for a target, i.e., the receptor. Peptides have the added advantage of small size, so they more readily permeate interstitial space, the blood brain barrier, tumorous masses, and even cell membranes. Where membrane translocation is desired, the chelating agent can be prepared to have predominantly hydrophobic character, as described in Section 5.1.2, supra. Thus peptides are effective for targeting radiometals to such locations. Similarly, steroids, which are also receptor-specific, small, and readily cross cell membranes, are useful targeting molecules depending upon the nature of the cellular disorder. Route of administration may be parenteral, with intravenous administration generally preferred.

5.4.2. IN VIVO DIAGNOSTICS

In vivo diagnostic applications involve imaging of specific tissues or cellular disorders by administration of a sufficient amount of the antibody-metal ion complexes of the invention to enable the complexes to localize at the tissue in the appropriate time frame. Dosage and other aspects of administration of the complexes in vivo are generally discussed in the preceding section.

A wide variety of metal ions suitable for in vivo tissue imaging have been tested and utilized clinically. For imaging with radioisotopes the following characteristics are generally recognized as desirable and/or necessary: (a) low radiation dose to the patient; (b) high photon yield which permits a nuclear medicine procedure to be performed in a short time period; (c) ability to be produced in sufficient quantities; (d) acceptable cost; (e) simple preparation for administration; and (f) no requirement for subsequent isolation from the patient. These characteristics generally translate into the following: (a) the radiation exposure to the most critical organ is less than 5 rad; (b) a single image can be obtained in several hours; (c) the radioisotope does not decay by emission of a particle (e.g., $\beta$- or B+); (d) the isotope can be readily detected; and (e) the half-life is less than four days. (Lamb and Kramer, "Commercial Production of Radioisotopes for Nuclear Medicine" IN Radiotracers For Medical Applications, Vol. 1, Rayudu (ed.), CRC Press, Inc., Boca Raton, pp. 17-62.) Preferably the metal is technetium-99m.

An alternative method for imaging with radioisotopes involves positron emission tomography. Suitable positron emitting isotopes include $^{43}$Scandium, $^{44}$Scandium, $^{52}$Iron, $^{55}$Cobalt and $^{68}$Gallium.

Tissue imaging may also utilize nonradioactive paramagnetic metal ions such as $^{54}$Iron, $^{56}$Iron, $^{57}$Iron, $^{58}$Iron, $^{157}$Gadolinium and $^{55}$Manganese, which are detectible by nuclear magnetic resonance spectroscopy.

Tissues which one may image include any solid neoplasm, certain organs such as lymph nodes, parathyroids, spleen and kidney, sites of inflammation or infection (e.g., macrophages at such sites), myocardial infarction or thromboses (neoantigenic determinants on fibrin or platelets), etc.

5.4.3. IN VITRO DIAGNOSTICS

In vitro analytical procedures for detecting a particular antigen using the antibody-metal ion complexes of the invention employ standard immunoradiometric assay techniques. For a general review of such techniques, see Hales and Woodhead, Methods in Enzymology 70:334-355 (1980). Generally immunoradiometric assays (IRA) involve labeled antibodies to detect unlabeled antigens. Numerous variations of the immunoradiometric assay have been developed, including for example, the two-site IRA and the indirect IRA. These two methods are discussed generally below.

The objective of the two-site IRA is to use a specific antibody on a solid phase, e.g., cellulose or Sepharose, to extract antigen. While the antibody remains bound to the solid phase, a second labeled antibody is bound to another site on the antigen. The antigen can then be measured as a function of the amount of bound labeled antibody. In this method the antigen is bound to two different antibodies at two sites on the antigen. In another method purified antigen is adsorbed or coupled to a solid phase support.

In the indirect IRA the (first) antibody used for measuring antigen is indirectly labeled through the use of a labeled antibody to the immunoglobulin of the same species as that in which the first antibody is raised. This labeled anti-immunoglobulin antibody is then reacted with the first antibody and antigen. The labeled antibody can also be used in the conventional or two site IRAs.

These diagnostic techniques and others are intended to be encompassed by the present invention.

In the context of this invention, all of these IRA methods for testing for antigen have in common the following two steps: (a) mixing an antibody-metal ion complex with a sample suspected of containing the antigen, and (b) detecting the interaction, if any antigen is present, of said complex with the antigen.

In the context of the invention, protein conjugates, peptide conjugates and nucleic acid conjugates can be used in place of antibody conjugates for detecting interaction with a receptor, ligand or complementary nucleic acid sequence (in place of antigen) in vitro.

For in vitro diagnostics, all of the gamma and positron emitting metal ions, as well as the paramagnetic metal ions in Section 5.4.2, as well as $^{153}$Gadolinium are suitable. For fluorescence diagnostic assays, lanthanides may be employed, including Praseodymium, Neodymium, Samarium, Europium, Gadolinium, Terbium, Dysprosium, Holmium, Erbium, Thulium and Ytterbium.

5.5. PHARMACEUTICAL COMPOSITIONS

The therapeutic or in vivo diagnostic agents of the invention can be prepared as pharmaceutical compositions by admixture with appropriate pharmaceutically acceptable carriers, diluents and adjuvants. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the patient. While intravenous injection is a very effective form of administration, other modes can be employed, including but not limited to intramuscular, intraventricular, intraarteriole, intraperitoneal, and subcutaneous injection, and oral, nasal and parenteral administration.

The therapeutic agents and diagnostic agents of the instant invention may be used for the treatment and/or diagnosis of animals, and more preferably, mammals, including humans, as well as mammals such as dogs, cats, horses, cows, pigs, guinea pigs, mice and rats.

The present invention will be made illustrated by the following Examples, which are provided by way of exemplification and not limitation.

6. EXAMPLE: PREPARATION OF 3,5-DI-(1-TRIMETHYLAMMONIUMACETYL)-4-THIOSEMICARBAZIDOBENZOIC ACID, DICHLORIDE SALT (CHELATING AGENT A)

6.1. 3,5-DIISOTHIOCYANATOBENZOIC ACID

A 500 ml one-neck round bottom flask was charged with 15.2 g (0.10 mol) of 3,5-diaminobenzoic acid (Aldrich), 175 ml of chloroform and 175 ml of water. Then, 17.0 ml (0,223 mol) of thiophosgene (Aldrich) was added to the resultant slurry at room temperature over a period of 15 min. The two phase, orange-red reaction mixture was allowed to stir for an additional 6 h at ambient temperature and then the aqueous layer was separated from the organic layer. The aqueous layer was extracted with two 100 ml portions of chloroform and then the organic layers were combined and washed with three 400 ml portions of water. The chloroform solution was dried over anhydrous magnesium sulfate, filtered, and the solvents were evaporated from the filtrate under vacuum to give 20.7 g (0,077 mmol, 88%yield) of 3,5-diisothiocyanatobenzoic acid; mp 125°–127° C.; $^1$H NMR (CDCl$_3$) δ7.81 (s, 2H), 7.27 (s, 1H).

6.2. CHELATING AGENT A

A 500 ml one-neck round bottom flask was charged at room temperature with 20.65 g (87.4 mmol) of 3,5-diisothiocyanatobenzoic acid, 175 ml of acetonitrile, 175 ml of water, and 31.0 g (185 mmol) of (carboxymethyl)trimethylammonium chloride hydrazide (Girard Reagent-T) (Aldrich). All solids in the reaction mixture dissolved over a period of approximately 2 h. The resultant solution was filtered through a pad of CELITE ® (Aldrich) and the solvents were evaporated from the filtrate at low pressure to leave an off-white solid residue. This residue was crystallized from 20% water in isopropanol to afford 40.0 g (70 mmol, 80% yield) of chelating agent A as a white solid; mp 198°–202° C.; $^1$H NMR (D$_2$O) δ7.89 (s, 2H), 7.69 (s, 1H), 4.28 (s. 4H), 3.36 (s, 18H).

Chelating agent A has the following structure:

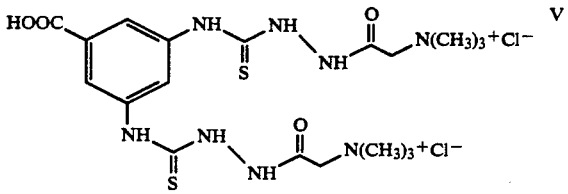

In chelating agent A, the carboxylic acid can be used as a linker for binding, e.g., to amine groups on a protein as shown in Section 9., infra, or can be modified, as shown in Section 7., infra, to form a nucleophilic linker.

For binding to electrophilic sites on targeting molecules.

7. EXAMPLE: PREPARATION OF A HYDRAZIDE LINKER ANALOG OF CHELATING AGENT A (CHELATING AGENT B)

7.1. PREPARATION OF N-BOC-6 AMINOCAPROIC ACID

A 250 ml round bottom flask was charged with 2.62 g (0.02 mol) of 6-aminocaproic acid (Aldrich), 40 ml of dioxane, 25 ml of water and 25 ml of 1.0N sodium hydroxide solution. The reaction solution was cooled to 0° C. and 4,583 g (0,021 mol) of di-tert-butyldicarbonate ($BOC_2O$) (Aldrich) was added. The reaction mixture was allowed to stir at 0° C. for 1.5 h and then most of the solvents were removed under vacuum to leave a liquid residue. This residue was dissolved in 30 ml of ethyl acetate, cooled to 0° C. for 10 min, and then 5% potassium hydrogen phosphate solution (approximately 50-60 ml) was added to bring the pH of the solution to between 2 and 3. The reaction solution was added to 50 ml of water and 30 ml of ethyl acetate. The aqueous layer was separated from the organic layer, and the aqueous layer was extracted with three 30 ml portions of ethyl acetate. The organic layers were combined, washed with two 75 ml portions of water, dried over $NaSO_4$, filtered, and the solvents were removed at reduced pressure to give 4.22 g (0.0182 mol, 91% yield) of N-BOC-6-aminocaproic acid as a thick yellow oil. $^1H$ NMR ($CDCl_3$) showed the peaks usually observed for 6-aminocaproic acid in addition to a large singlet at 1.48 ppm (tBu group).

7.2. PREPARATION OF N-BOC-6-AMINOCAPROIC ACID, N'-FMOC(FLOURENYLMETHOXYCARBONYL)HYDRAZIDE

A 250 ml round bottom flask was charged with 4,190 g (0.0181 mol) of N-BOC-6-aminocaproic acid, 4.60 g of 9-fluorenylmethyl carbazate (FMOC), (prepared by the method of Carpino et. al., 1972, *J. Org. Chem.*, 37:3404) and 35 ml of N,N-dimethylformamide. The reaction solution was cooled to 0° C. and then 3.75 g (0.0182 mol) of 1,3-dicyclohexylcarbodiimide (Aldrich) was added. The reaction mixture was allowed to stir for 2 h at 0° C. The white precipitate which formed during this time was filtered off and the solvents evaporated under reduced pressure. The distillation residue was applied to a 225 cc pad of silica gel (Merck), which was then washed with 1L of chloroform. The product was then eluted from the column using 1L of 50% methanol in chloroform. The solvents were evaporated from the desired eluent fractions to give 4.98 g (0.011 mol, 59% yield) of N-BOC-6-aminocaproic acid (N'-FMOC-hydrazide) as a yellow oil. $^1H$ NMR (DMSO-$d_6$) showed the peaks observed in the starting material and new protons in the aromatic region between 7-8 ppm (FMOC group).

7.3. PREPARATION OF 6-AMINOCAPROIC ACID N'-FMOC HYDRAZIDE

Using anhydrous conditions and under a nitrogen gas blanket, a 200 ml round bottom flask was charged with 4.90 g (10.48 mmol) of N-BOC-6-aminocaproate (N-(FMOC) hydrazide), and 10 ml of methylene chloride. The reaction mixture was then stirred at room temperature as 16 ml of trifluoroacetic acid (Schweizerhall) dissolved in 16 ml of methylene chloride was slowly added. The resultant homogeneous solution was allowed to stir for an additional 2 h and then 15 ml of toluene was added. The solvents and any remaining trifluoroacetic acid were then distilled off under reduced pressure. The distillation residue was twice more azeotroped with 15 ml portions of toluene to leave 8.49 g of orange oil. $^1H$ NMR showed this crude material to contain the peaks associated with aminocaproic acid and a FMOC substituent. However, no tert-butyl peak was observed between 1-2 ppm showing removal of the BOC protecting group. This product was used without further purification.

7.4. PREPARATION OF THE 6-AMINOCAPROIC ACID, N'-FMOC HYDRAZIDE DERIVATIVE OF CHELATING AGENT A

A 250 ml round bottom flask was charged, under a blanket of dry nitrogen gas, with 2,909 g of chelating agent A (Section 6, supra) and 35 ml of dry N,N-dimethylformamide. The reaction flask was then cooled to 0° C. and 1.33 ml (7.64 mmol) of N,N-diisopropylethylamine (Aldrich) followed by 660 ml (5.09 mmol) of isobutylchloroformate (Aldrich) were added. The reaction mixture was allowed to stir at 0° C. for one hour and then 2.45 g of crude 6-amino caproate (N'-FMOC-hydrazide), dissolved in 12 ml of N,N-dimethylformamide and 2.66 ml (15.28 mmol) of N,N-diisopropylethylamine (Aldrich) was added. The reaction mixture became bright yellow and stirring was continued for 1 h at 0° C., and a further 2 h at ambient temperature. The reaction solution was then filtered, and the solvents were evaporated at reduced pressure to leave a thick oil which was purified by preparative HPLC (RP-18 Waters-Millipore Column, 5×30 cm, $H_2O/CH_3CN$, 0.1% TFA, gradient elution) to give 1.787 g (38% cumulative yield for the last two synthetic steps) of the 6-aminocaproic acid, (N'(FMOC) hydrazide) derivative of chelating agent A as a white solid. $M^+ = 849$. $^1H$ NMR (DMSO) δ7.30-8.00 (m, 11H), 4.20-4.50 (m, 4H), 4.19-4.50 (s, 4H), 3.28 (s, 18H), 1.3-2.2 (m, 8H).

7.5. PREPARATION OF CHELATING AGENT B

A 250 ml round bottom flask was charged, under a nitrogen blanket, with 1.646 g (1.79 mmol) of the 6-aminocaproic acid, N'-(FMOC) hydrazide derivative of chelating agent A, 25 ml of N,N-dimethylformamide, and 1.78 ml (18 mmol) of piperidine (Aldrich). The reaction mixture was allowed to stir at ambient temperature for 2 h and then the solvents were distilled under reduced pressure to leave a residue which was dissolved in a mixture of 200 ml of water and 150 ml of diethyl ether. The organic layer was separated from the aqueous layer and the organic layer was extracted with two 50 ml portions of water. The aqueous layers were combined, washed with three 150 ml portions of ether, and the solvents were removed at reduced pressure to give 0.800 g (1.145 mmol, 64% yield) of chelating agent B as a colorless glass. $^1H$ NMR (DMSO-$d_6$) δ7.75 (s, 2H), 7.53 (s, 1H), 3.20-3.4 (m, 8H) 3.00 (bs, 18H), 1.20-2.05 (m, 6H).

Chelating agent B has the following structure:

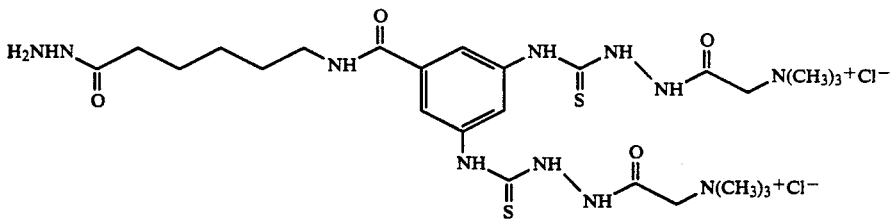

VI

The hydrazide linker of chelating agent B is particularly suited for conjugation with oxidized glycoproteins, especially oxidized antibodies, as shown in Section 10.

8. EXAMPLE: PREPARATION OF 3, 4 -DI-(1-METHYLTHIOFORMAMIDO)-4-THIOSEMICARBAZIDO) BENZOIC ACID, METHYL ESTER (CHELATING AGENT C )

8.1. PREPARATION OF 5-BENZIMIDAZOLE-CARBOXYLIC ACID, METHYL ESTER

A 500 ml round bottom flask equipped with a heating mantle, reflux condenser, and a Drierite$^R$filled drying tube was charged with 16.22 g (0.10 mol) of 5-benzimidazolecarboxylic acid (Aldrich), 400 ml of anhydrous methanol and then (Caution!) 20 ml of concentrated sulfuric acid (Fisher). The reaction mixture was heated to reflux for 18 h and then cooled to ambient temperature.

Approximately 75% of the solvents were removed under vacuum and then the remaining liquid residue was slowly poured into 500 ml of saturated sodium bicarbonate solution. The resultant two phase system was then extracted with three 250 ml portions of ethyl acetate. The organic layers were combined and washed with three 250 ml portions of 5% sodium bicarbonate solution followed by one 250 ml portion of brine. The ethyl acetate layer was dried over MgSO$_4$, filtered and the solvents were then removed under reduced pressure to give 15.68 g (0,089 mol, 89% yield) of 5-benzimidazolecarboxylic acid, methyl ester, as a tan solid. $^1$H NMR (CDCl$_3$) $\delta$7.3–7.9 (m, 3H), 3.70 (s, 3H).

8.2. PREPARATION OF 3,4-DIISOTHIOCYANATOBENZOIC ACID, METHYL ESTER

A 250 ml round bottom flask was charged with 4.98 g (50 mmol) of calcium carbonate, 10 ml of methylene chloride, and 3 ml of water. The resultant slurry was cooled to 10° C. and then 2.27 ml (3.43 g, 30 mmol) of thiophosgene (Aldrich) followed by 2.50 g (14.2 mmol) of 5-benzimidazolecarboxylic acid, methyl ester, dissolved in 50 ml of a 1:1 mixture of acetonitrile in water were slowly added. The reaction mixture was stirred for 4 h and the temperature was allowed to rise to 15°–20° C. The orange-white reaction slurry was then filtered and the filtrate was washed with three 50 ml portions of methylene chloride. The organic layers were combined, dried over MgSO$_4$, filtered, and the solvents were removed under vacuum to leave a beige residue. This residue was triturated four times with petroleum ether to leave, after drying for 16 h at 25° C. at 30 mm pressure, 2.14 g (8.56 mmol, 60% yield) of 3,4-diisothiocyanatobenzoic acid, methyl ester, as an off-white powder. $^1$H NMR (CDCl$_3$) $\delta$7.85–7.95 (m, 2H), 7.30 (d, 1H), 3.92 (s, 3H). IR showed a doublet (NCS) at 2140 cm$^{-1}$.

8.3. PREPARATION OF CHELATING AGENT C

A 50 ml round bottom flask was charged with 0.25 g (1.0 mmol) of 3,4-diisothiocyanatobenzoic acid, methyl ester, 25 ml of acetonitrile, and 0,210 g (2 mmol) of 4-methyl-3-thiosemicarbazide (Aldrich). The reaction mixture was allowed to stir at ambient temperature for 16 h during which time a white precipitate formed. The precipitate was then filtered, washed with 25 ml of acetonitrile, and dried at 25° C. at 20 mm pressure to give 0.29 g (0.63 mmol, 63% yield) of chelating agent C as a white powder. $^1$H NMR (DMSO-d$_6$) $\delta$7.79 (d, 1H), 7.67 (s, 1H), 7.20 (d, 1H), 3.85 (s, 3H), 3.35 (s, 6H). MH+ =461.

The chelating agent C has the following structure:

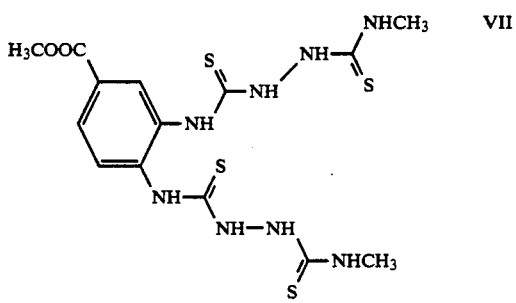

VII

Chelating agent C is suited for coupling to an amine on a peptide or protein group after hydrolysis of the methyl ester and coupling of the resultant free acid to the amino group by standard coupling methods, e.g., carbodiimide. In addition, the methyl ester can be converted by hydrazinolysis to the corresponding acid hydrazide which is useful for coupling site specifically (vida supra). A particular advantage of chelating agent C is the presence of four thiocarbonyls to chelate a radiometal.

9. PREPARATION OF A PEPTIDE CONJUGATE AND ISOTOPE LABELING

9.1. COUPLING OF CHELATING AGENT A WITH SYRGDVRGDF-NH$_2$ PEPTIDE

Under anhydrous conditions, a 20 ml reaction vial was charged with 7.0 mg (12.24 mmol) of chelating agent A, 5.9 ml of dry N,N-dimethylformamide, 3.7 mg (28.7 mmol) of N,N-diisopropylethylamine, and 74 ml (37.0 mmol) of a 0.5M solution of HBTU/HOBt(2-(1H-Benzotriazol-1-yl)-1,1,3,3-tetramethyl uronium hexafluorophosphate and 1-hydroxybenzotriazole, respectively) in N,N-dimethylformamide (Applied Biosystems). The reaction mixture quickly became bright yellow and was allowed to stand at ambient temperature for 0.5 h. A 1.55 ml aliquot of this solution was then added to a reaction vial which contained 3.0 mg (2.0 mmol) of SYRGDVRGDF-NH$_2$ peptide. The resultant solution was allowed to stand at ambient temperature for 3 h and then the solvents were evaporated at reduced pressure. The peptide conjugate product (the new peak observed on an analytical HPLC trace) was isolated (2.4 mg, 1.2 mmol, 60% yield) by preparative HPLC (Waters-Millipore RP-18, 19 mm×30 cm SS column) using a water/acetonitrile gradient elution. The conjugate isolated showed the expected peptide profile upon amino acid analysis.

9.2. LABELING OF PEPTIDE CONJUGATE WITH TC-99M

A freshly prepared mixture containing 4.0 mg of peptide conjugate product dissolved in 20 nM sodium acetate at pH 4.5 was passed through a 0.22 μ cellulose acetate filter into a glass test tube. A solution of 200 mCi of Tc-99m (prepared by adding sodium pertechnetate to a "GLUCOSCAN KIT") was then added to the test tube and allowed to incubate for 90 min at 37° C. One microliter of the incubated material was spotted onto a silica gel impregnated instant thin layer chromatography (ITLC) glass fiber sheet. The ITLC sheet was then placed into a 10 ml glass vial containing 1.5 ml of 0.9% saline solution. The chromatography was allowed to proceed for 1.5 min and the ITLC strip was then removed and allowed to dry. The strip was cut in half, and both the top and bottom portions were counted in a LKB gamma radiation counter. The percent of gamma radiation remaining on the bottom of the ITLC strip was designated as the "percent incorporation." The conjugate was also incubated with increasing amounts of Tc-99m-GLYCOSCAN to assay its chelating capacity.

9.3. RESULTS OF RADIOLABELING

The peptide conjugate complex does not move on the ITLC plate (confirmed with a spray peptide detection reagent), but the Tc-GLUCOSCAN does. Thus, by measuring the gamma radiation at the top and bottom of the ITLC plate, a quantitative figure for the amount of Tc incorporation in the peptide-chelating agent conjugate can be calculated. The results follow:

|  | cpm |
| --- | --- |
| Bottom of ITLC Strip: | 1752221.2 |
| Top of ITLC Strip: | 117530.0 |

Percent of TC$^{99}$m Incorporation onto peptide chelator conjugate: 94%.

A representative ITLC autoradiogram from another experiment is shown in FIG. 1. FIG. 2 shows the capacity of chelating agent A conjugated to the peptide to chelate Tc-99m. The results show a capacity of between 50 and 100 μCi per ng of chelating agent A-peptide conjugate.

10. EXAMPLE: PREPARATION AND Tc-99m RADIOLABELING OF AN ANTIBODY CONJUGATE

10.1. MATERIALS AND METHODS
10.1.1. OXIDATION PROCEDURE

The oxidation of antibody B 72.3 ("antibody") was accomplished using the oxidation procedure taught in U.S. Pat. No. 4,741,900. This antibody is specific for a human mammary tumor antigen (Antibody B72.3, Colcher et al., 1981, Proc. Natl. Acad. Sci. U.S.A. 78:3199–3203. Specifically, a 383-fold molar excess of m-sodium periodate to antibody was used. The antibody was in solution at 6.2 mg/ml, phosphate buffered saline (PBS), pH 6. The mixture was incubated in the dark for 1 hour at room temperature.

The excess periodate was then removed by using gel-filtration chromatography on a acrylamide resin ("Speedy" column, Pierce Chemical Co.) that had been equilibrated with 0.1M acetate buffer at pH 5.0. The oxidized antibody was concentrated to 4.73 mg/ml in the 0.1M acetate buffer, pH 5, using the Centricon-30 (Areicon).

10.1.2. CONJUGATION PROCEDURE

The conjugations were run with the oxidized antibody concentration at approximately 5 mg/ml in 0.1 M acetate buffer pH 5. Chelating agent B (Section 7, supra) was prepared in the acetate buffer and added in either a 1× or 3× molar excess over the number of aldehydes per molecule of oxidized antibody.

The conjugations were incubated overnight at room temperature with mixing by inversion. The individual conjugation reaction mixes were each purified by HPLC with a glass TSK G3000SW column run in PBS, pH 6 at a flow rate of 0.5 ml/minute with monitoring of the UV absorbance at 280 and 300 nm. Fractions were collected each minute over the 35 minute run. The collected fractions corresponding to the IgG peak were quickly read at 280 nm and the appropriate fractions were combined, total volumes measured and protein concentrations determined.

Each conjugate was then concentrated on the Amicon stirred cell apparatus to 2.0–2.5 mg/ml in the PBS pH 6 buffer and stored at 2°–8° C. in microcentrifuge tubes.

10.1.3. Tc-99m RADIOLABELING PROCEDURE

Radiolabeling was done using the established Tc-99m-GLUCOSCAN method. The reduced Tc-99m was added to the prepared conjugates in the PBS pH 6 buffer. The samples were incubated at room temperature for 1 hour and the percent incorporation was determined by ITLC (see Section 9.2, supra) developed in saline. The samples were also analyzed by HPLC on a TSK G3000SWXL in PBS pH 6 at 1.0 ml/minute. Fractions were collected at 0.4 minute intervals beginning at 5.0 minutes after injection. The collected fractions were counted on a gamma counter and profiles plotted to correlate the radioactivity peaks to the protein peaks.

10.2. RESULTS

Results from the HPLC runs are shown in FIGS. 3 and 4. These runs show that the radioactivity is associated with the IgG in the oxidized antibody-chelating agent B conjugates. Negative controls of oxidized antibody alone and oxidized antibody mixed with the non-reactive chelating agent A compound show that the radioactivity is associated only with the salt peaks where the compound elutes and not at all with antibody (FIG. 5).

11. EXAMPLE: BIODISTRIBUTION OF Tc-99m-LABELED CHELATORS

To show that a chelating agent-Tc-99m complex of the invention has normal biodistribution characteristics, a biodistribution assay was performed. As a control, Tc-99m-GLUCOSCAN was used. A sample of Tc-99m-GLUCOSCAN or chelating agent A-Tc-99m was injected in a BALB/c mouse. The animal was a normal, without any tumors. Biodistribution was measured by quantitating the amount of radioactivity (CPM) per gram of organ and normalized to the amount of radioactivity (CPM) per gram of blood. Radioactivity was measured 4 and 23 hours after injection. The results are shown in FIG. 6. The results show that chelating agent A-Tc-99m complex has similar biodistribution properties as Tc-99m-GLUCOSCAN.

12. EXAMPLE: IMAGING OF A TUMOR WITH TC-99M-LABELED ANTIBODY

The biodistribution of the Tc-99m-labeled antibody-chelating agent B conjugate prepared in Section 10, supra, was assayed. A murine tumor was specifically targeted by the conjugate, and was imaged with a gamma camera.

12.1. MATERIALS AND METHODS

LS174T tumor-bearing nude mice received about 500 μCi of Tc-99m-labelled antibody chelating agent B conjugate on day 0. Control mice received a mixture of the antibody (20 μg) and Tc-99m-labeled chelating agent B (500 μCi) that were not conjugated. Tc-99m labeling followed the conjugation procedure described in Section 10., supra.

Mice were injected retroorbitally and counted in a dose calibrator immediately after injection. The spent syringes were also weighed and counted. All mice within the group were dose calibrated for Tc-99m following injection, and only mice within 70% of the mean were followed. Animals were observed after dosing and once daily for appearance, behavior, excretory function and discharges, and were weighted to within 0.1 gram.

Two mice from each group were imaged 4 and 24 hours post injection. Blood was also obtained from the retroorbital venous sinus opposite to the one used for injection at various times after injection.

Immediately prior to dissection, the tumor in each animal can be measured. A 250 μl blood sample is obtained via the retroorbital venous sinus, opposite the one used for injection, and weighed. The following organs are weighed to the nearest milligram after careful dissection to remove extraneous tissue: (1) blood, (2) lung, (3) spleen, (4) liver, (5) right kidney, (6) left kidney, (7) tumor, (8) muscle, and (9) femur.

12.2. RESULTS

The gamma camera image of a mouse injected with the Tc-99m-labeled antibody-chelating agent B conjugate is shown in FIG. 7. Three hours post injection, the tumor is clearly visible against background (FIG. 7a). Twenty-½ hours after injection the tumor is still clearly visible (FIG. 7b) and the background signal has decreased substantially by this time.

12.3. CONCLUSION

Chelating agents of the invention can be used to label a targeting molecule, e.g., an antibody, for imaging. As shown here, a tumor can be imaged in a murine model system.

The gamma camera results show that the Tc-99m non-specific signal from the kidneys is relatively low. This result is especially gratifying because frequently Tc-99m localizes non-specifically to kidney.

13. EXAMPLE: THROMBUS IMAGING WITH A PEPTIDE-CHELATING AGENT A CONJUGATE

The specificity of uptake of Tc-99m labeled peptide SYRGDVRGDF-chelating agent A conjugate into rabbit thrombi was determined by directly comparing tissue uptake and images obtained in animals with an induced thrombus to those receiving a sham operation without induced thrombus.

13.1. MATERIALS AND METHODS

Two groups of 3 rabbits were used. All animals were subjected to surgery to expose the superficial jugular vein as described in detail below. In the first group of animals, the jugular veins were clamped off and a silk thread was inserted into the jugular veins. These veins also received an injection of 10 units of bovine thrombin in 0.1 ml isotonic saline directly into the vein. The second (sham control) group of animals was subjected to the same surgical procedures as the experimental group except that no silk was inserted into the veins of these animals and the veins received an injection of 0.1 ml isotonic saline only. Due to logistical difficulties in handling six animals at one time, the experiment was conducted in three parts, each part consisting of one sham and one thrombus-induced animal done in parallel on each of 3 days. Specific pathogen-free New Zealand White rabbits (2–2.6 kg) were used.

Rabbits were grouped for testing as shown in Table I.

TABLE I

| | | | Group Assignments | | | |
|---|---|---|---|---|---|---|
| | | | Tc-99m peptide-chelator mg | Tc-99m peptide-chelator mCi | Time of: | |
| Group | # of Rabbits | Thrombus | | | Image | Dissect |
| 1 | 5 | yes | 50 | 6 | 5 min, 1 h, 2 h, 4 h | 4 h |
| 2 | 3 | no | 50 | 6 | 5 min, 1 h, 2 h, 4 h | 4 h |

The model system of Collen et al. (1983, J. Clin. Invest. 71:368–376) was used (with minor modifications described below) to induce experimental thrombi in rabbits. The animals were anesthetized by intramuscular injection of 40 mg/kg ketamine-HCl and 4 mg/kg acepromazine maleate. Just prior to surgery, the animals received 10 mg/kg sodium pentobarbital, which was also administered as needed during the course of the surgery. The neck area was shaved and swabbed with disinfectant. The jugular vein was exposed by making about a 5 cm paramedial incision, the vein was freed from tissues over about a 4 cm distance (up to the main bifurcation of the facial vein) and the side branches of the jugular were ligated. A 1-inch segment was clamped off with hemostats and, in the experimental (group 1) animals, a silk thread was placed longitudinally inside the vein and was tied off at each end. No suture was placed in the veins of sham control (group 2) animals. Ten (10) units of bovine thrombin in 0.1 ml of isotonic saline (or saline alone in sham control animals) was injected into the clamped vein segment using a 27 gauge needle. Thirty minutes later, the animals were given an intravenous injection (in the contralateral marginal ear vein) of a mixture of 2–7 μCi of Tc-99m labelled peptide-chelating agent conjugate.

The peptide-chelating agent conjugate prepared as in Section 9, supra, was radiolabeled with Tc-99m as follows: Tc-99m was eluted from a molybdenum generator and adjusted to 40 mCi/ml with isotonic saline. Fifty (50) mCi of this preparation was transferred to a Glucoscan vial (Dupont, Billerica, MA) and mixed. Six (6) mCi of Tc-99m/glucoscan mixture was then added to a vial containing 50 μg of the peptide-chelating agent conjugate and incubated for 1 h at room temperature. After this incubation period the material was drawn into an appropriately labelled 5 ml syringe and a sample was analyzed by instant thin layer chromatography (ITLC) to determine radiochemical purity as described in Section 9, supra. This material was acceptable for injection into rabbits only if the radiochemical purity was ≧95% and the amount of radioactivity available for injection was within 20% of that required by this protocol (e.g., 4.8-7.3 mCi).

Three (3) ten μl samples of each injectate were saved for subsequent gamma counting and decay correction.

Each syringe containing test material was counted in a dose calibrator set to quantitate Tc-99m. Animals were injected via a butterfly catheter inserted into the contralateral marginal ear vein. The animals were injected first with peptide-chelating agent A conjugate Tc-99m, after which the catheter was flushed with 2-5 ml saline. The time of each injection (to the nearest minute) was recorded in the experimental notebook. The body weight of each animal was recorded to the nearest 10 grams prior to use.

The animals were monitored for gross adverse effects at least hourly from the time of infusion up until the time of sacrifice. Any adverse effects or mortality were recorded. Animals not expected to survive to the next observation period were euthanized.

Images were obtained at 5 min, 1 h, 2 h and 4 h post-injection. Before injection, the animal was positioned for obtaining an anterior view of the chest, using a large field of view gamma camera (General Electric, Milwaukee, Wis., U.S.A.). The camera was fitted with a low energy, all purpose collimator set to acquire the 140 KeV radiation with a 20% window. A Macintosh IIx computer was interfaced to the camera using a Nuclear Mac A/D board and software (Scientific Imaging, Denver, Colo., U.S.A.). Initially the computer was set to acquire a dynamic series of 10 second frames for a total of 10 minutes. The acquisition was begun just before injection of the radiotracers. At the indicated intervals, 10 second static, anterior views of the chest were acquired. These images were used to determine the rate of clearance of radioactivity from the blood. In each frame, a region of interest was drawn around the heart. The counts in the region of the heart were corrected for decay and expressed as a percentage of the maximum counts in the heart region. Immediately after completion of the initial dynamic acquisition, and at approximately hourly intervals thereafter, rabbits were repositioned to obtain anterior views of the head and neck. Static images were acquired in a 256×256 matrix and 500,000 counts were accumulated.

Photographs and/or films of the images obtained can be evaluated in a blinded fashion by three separated readers who do not know what reagent the animal was injected with or whether the animal was from group 1 (experimental) or group 2 (sham) at the time the images were read. The following scale can be used to evaluate the images:

| Interpretation | Score |
| --- | --- |
| No image observed | 0 |
| Slight image/low confidence that localization occurred | 1 |
| Moderate image/moderate confidence that image occurred | 2 |
| Clearly discernable image/high confidence that localization occurred | 3 |

All animals were dissected 4 h (240 min) after injection. A 3 ml blood sample was drawn, after which the animals were euthanized with an i.v. injection of T-61 euthanasia solution (American Hoechst, Sommerville, N.J.). The vein segment was surgically removed and the thrombus therein (if any) was isolated from the vein. A segment of the contralateral vein was also removed and a sample of muscle was obtained from an area of the neck distal to the surgical field. The following tissues were weighed to the nearest milligram on an electronic analytical balance following careful dissection and trimming to remove extraneous tissue:

| | |
| --- | --- |
| Clot (Target) | Thread (Inside vein portion) |
| Vessel | Thread (Outside vein portion) |
| Blood | Contralateral vein sample |
| Muscle | |

In cases where the clot was observed to propagate along the ear vein, additional samples of this vein were taken.

The dissected organs were placed into numbered test tubes and weighed. These tubes were transferred to racks and the radioactivity in them was determined by gamma counting.

13.2. RESULTS

Gamma camera imaging (FIG. 8) shows localization of Tc-99m-labeled SYRGDVRGDF-chelating agent A conjugate to a clot in the area of the arrow 2 hours (FIG. 8a) and 4 hours (FIG. 8b) after the procedure. The area of the head is dark, reflecting blood pool accumulation of peptide-chelating agent A, which is non-specific. The results in Table II show specific localization of Tc-99m-labeled peptide-chelating agent A conjugate to the clot. The relative targeting is reflected by the percent of injected dose per gram of tissue (% ID/G). For the clot, this value was 0.33%, 4-fold greater than the blood vessel and 8-fold greater than blood.

TABLE II

BIODISTRIBUTION RESULTS (CHELATOR A)
BLOOD CLOT WITH Tc-99m PEPTIDE-CHELATING AGENT A

| SAMPLE | NET SPL WT | 99M Tc | % ID/G | TISS:BLD | TISS:MUSC |
| --- | --- | --- | --- | --- | --- |
| Clot (Target) | 0.0996 | 94319 | 0.3312 | 28.30 | 27.83 |
| Vessel | 0.0439 | 95629 | 0.0870 | 2.18 | 7.28 |
| Blood | 0.3182 | 318229 | 0.0399 | | |
| Muscle | 0.0746 | 22369 | 0.0119 | | |
| Background | | 26 | | | |

[1]Percent of injected does per gram of tissue.

Data from an aggregometer assay (performed as described in Zucker, 1989, Meth. Enzymol. 169:117, incorporated herein by reference in its entirety) shows full or even enhanced clot-binding potency of the peptide-chelating agent A conjugate relative to the native peptide as shown in Table III.

TABLE III

AGGREGOMETER ASSAY

| Peptide | $IC_{50}$ (μM) |
| --- | --- |
| SYRGDVRGDF | 28.8 |
| Chelating Agent A-NH-SYRGDVRGDF | 19.3 |

13.3. CONCLUSIONS

The foregoing example clearly demonstrates that a peptide-chelator conjugate of this invention can be used to image in vivo. In particular, these data demonstrate that peptides such as SYRGDVRGDF can target in vivo, e.g., to activated platelets, and should be useful for imaging blood clots.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A chelating agent of the formula:

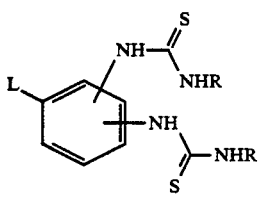

in which NHCSNHR is in the 2,3- or 3,4-positions, and R is H or a substituent of the general formula:

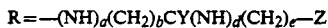

in which
a=0 or 1;
b=0-10;
CY is C=S, C=O or CH$_2$;
d=0-2;
e=1-10;
Z= is H, N(R')$_3$+X$^-$, SO$_3$H, CO$_2$H, OH, H$_2$PO$_3$; in which X$^-$ is a counterion such as a halide or an acid salt and R' is a C$_1$ to C$_4$ lower alkyl; and
L comprises a reactive linker group selected from the group consisting of a primary amine, hydrazide, acid hydrazide, thioacid hydrazide, semicarbazide, thiosemicarbazide, reactive disulfide group, p-mercuribenzoate group, maleimide group, carboxylic acid, a carboxylic acid ester, an isothiocyanate, and succinate.

2. The chelating agent of claim 1 in which the NHCSNHR groups are in the 3,4-positions.

3. The chelating agent of claim 1 in which L is spaced from 0 to about 20 atoms from the benzene ring.

4. The chelating agent of claim 1 in which the reactive group of L is selected from the group consisting of a primary amine, hydrazide, acid hydrazide, thioacid hydrazide, semicarbazide or thiosemicarbazide.

5. The chelating agent of claim 1 in which the reactive group of L is selected from the group consisting of a reactive disulfide group, a p-mercuribenzoate group and a maleimide group.

6. The chelating agent of claim 1 in which the reactive group of L is selected from the group consisting of a carboxylic acid, a carboxylic acid ester, an isothiocyanate, and a succinate.

7. The chelating agent of claim 1 in which R is:

in which
a=0 or 2,
e=1-10,
CY is C=S, C=O or CH$_2$; and
Z is H, N(R')$_3$+X$^-$, SO$_3$H, CO$_2$H, OH, H$_2$PO$_3$; in which X$^-$ is a counterion such as a halide or an acid salt and R' is a C$_1$ to C$_4$ lower alkyl.

8. The chelating agent of claim 7 in which Z is selected from the group consisting of an amine or salt thereof, an acid or a salt thereof, and a hydroxy group.

9. The chelating agent of claim 8 in which the amine-salt is trimethylammonium chloride, trimethylammonium acetate, or trimethylammonium trifluoroacetate.

10. A complex comprising the chelating agent of claim 1 and a metal ion.

11. The complex of claim 10 in which the metal ion is an isotope selected from the group consisting of technetium, rhenium, copper, mercury, lead and bismuth.

12. The complex of claim 11 in which the metal ion is technetium-99m.

13. A conjugate comprising the chelating agent of claim 1 and a targeting molecule capable of specific interaction with a target molecule, said targeting molecule selected from the group consisting of an antibody, a protein, a peptide, a nucleic acid, and a steroid.

14. The conjugate of claim 13 in which the targeting molecule is an antibody, an Fab fragment of an antibody, or an F(ab')$_2$ fragment of an antibody.

15. The conjugate of claim 13 in which the targeting molecule is a peptide.

16. The conjugate of claim 13 in which the targeting molecule is protein.

17. The complex comprising the conjugate of claim 13 and a metal ion.

18. The complex of claim 17 in which the metal ion is an isotope selected from the group consisting of technetium, rhenium, copper, mercury, lead and bismuth.

19. The complex of claim 18 in which the metal ion is technetium-99m.

20. A chelating agent of the formula:

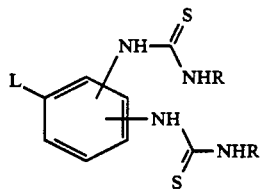

in which the NHCSNHR groups are in the 2,4- or 3,5-positions; and R is hydrogen or a substituent of the general formula:

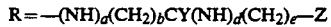

in which
a=0 or 1;
b=0-10;
CY is C=S, C=O or CH$_2$;
d=0-2;
e=1-10;
Z= is H, N(R')$_3$+X$^-$, SO$_3$H, CO$_2$H, OH, H$_2$PO$_3$; in which X$^-$ is a counterion such as a halide or an acid melt and R' is a C$_1$ to C$_4$ lower alkyl; and
L comprises a reactive linker group selected from the group consisting of a primary amine, hydrazide, acid hydrazide, thioacid hydrazide, semicarbazide, thiosemicarbazide, reactive disulfide group, p-mercuribenzoate group, maleimide group, carboxylic acid, a carboxylic acid ester, an isothiocyanate, and succinate.

21. The chelating agent of claim 20 in which the NHCSNHR groups are in the 3,5-positions.

22. The chelating agent of claim 20 in which L is spaced from 0 to about 20 atoms from the benzene ring.

23. The chelating agent of claim 20 in which the reactive group of L is selected from the group consisting of a primary amine, hydrazide, acid hydrazide, thioacid hydrazide, semicarbazide or thiosemicarbazide.

24. The chelating agent of claim 20 in which the reactive group of L is selected from the group consisting of a reactive disulfide group, a p-mercuribenzoate group and a maleimide group.

25. The chelating agent of claim 20 in which the reactive group of L is selected from the group consisting of a carboxylic acid, a carboxylic acid ester, an isothiocyanate, and a succinate.

26. The chelating agent of claim 39 in which R is:

in which
a=0–2,
e=0–10,
CY is C=S, C=O or $CH_2$; and
Z is H, $N(R')_3{}^+X^-$, $SO_3H$, $CO_2H$, OH, $H_2PO_3$; in which $X^-$ is a counterion such as a halide or an acid salt and R' is a $C_1$ to $C_4$ lower alkyl.

27. The chelating agent of claim 26 in which Z is selected from the group consisting of an amine or salt thereof, an acid or a salt thereof, and a hydroxy group.

28. The chelating agent of claim 27 in which the amine-salt is trimethylammonium chloride, trimethylammonium acetate, or trimethylammonium trifluoroacetate.

29. A complex comprising the chelating agent of claim 20 and a metal ion.

30. The complex of claim 29 in which the metal ion is an isotope selected from the group consisting of technetium, rhenium, copper, mercury, lead and bismuth.

31. The complex of claim 30 in which the metal ion is technetium-99m.

32. A conjugate comprising the chelating agent of claim 20 and a targeting molecule capable of specific interaction with a target molecule, said targeting molecule selected from the group consisting of an antibody, a protein, a peptide, a nucleic acid, and a steroid.

33. The conjugate of claim 32 in which the targeting molecule is an antibody, an Fab fragment of an antibody, or an F(ab')₂ fragment of an antibody.

34. The conjugate of claim 32 in which the targeting molecule is a peptide.

35. The conjugate of claim 32 in which the targeting molecule is a protein.

36. A complex comprising the conjugate of claim 32 and a metal ion.

37. The complex of claim 36 in which the metal ion is an isotope selected from the group consisting of technetium, rhenium, copper, mercury, lead and bismuth.

38. The complex of claim 37 in which the metal ion is technetium-99m.

39. The chelating agent of claim 4 in which L is —$CONH(CH_2)_5CONHNH_2$.

40. The chelating agent of claim 23 in which L is —$CONH(CH_2)_5CONHNH_2$.

41. The chelating agent of claim 6 in which L is a carboxylic acid or a carboxylic acid methyl ester.

42. The chelating agent of claim 25 in which L is a carboxylic acid or a carboxylic acid methyl ester.

43. The chelating agent of claim 20 in which R is

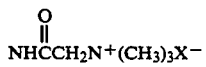

in which $X^-$ is a halide ion; and L is an acid hydrazide.

44. A conjugate comprising the chelating agent of claim 43 and a targeting molecule which is an antibody, an Fab fragment of an antibody or an F(ab')₂ fragment of an antibody.

45. A complex comprising the conjugate of claim 44 and a metal ion in which the metal ion is technetium.

* * * * *